(12) United States Patent
Kamatani et al.

(10) Patent No.: US 8,951,648 B2
(45) Date of Patent: Feb. 10, 2015

(54) DIACENAPHTHO[1,2-B:1',2'-K]CHRYSENE DERIVATIVE

(75) Inventors: Jun Kamatani, Tokyo (JP); Masashi Hashimoto, Tokyo (JP); Naoki Yamada, Inagi (JP); Akihito Saitoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 444 days.

(21) Appl. No.: 13/140,809

(22) PCT Filed: Dec. 16, 2009

(86) PCT No.: PCT/JP2009/071367
§ 371 (c)(1),
(2), (4) Date: Jun. 17, 2011

(87) PCT Pub. No.: WO2010/071224
PCT Pub. Date: Jun. 24, 2010

(65) Prior Publication Data
US 2011/0251446 A1    Oct. 13, 2011

(30) Foreign Application Priority Data
Dec. 19, 2008   (JP) ................ 2008-324468

(51) Int. Cl.
*C07C 13/62*    (2006.01)
*H01L 51/54*    (2006.01)
(Continued)

(52) U.S. Cl.
CPC ............. *C09K 11/06* (2013.01); *C07C 13/62* (2013.01); *C07C 211/61* (2013.01); *C07D 213/06* (2013.01); *C07D 239/26* (2013.01); *H01L 51/0054* (2013.01); *H01L 51/0057* (2013.01); *H01L 51/0058* (2013.01); *H05B 33/14* (2013.01); *C07C 2103/18* (2013.01);
(Continued)

(58) Field of Classification Search
CPC .. C07C 13/62; C07C 211/61; C07C 2103/18; C07C 2103/54; H05B 33/14; C07D 239/26; C09K 11/06; C09K 2211/1011; C09K 2211/1014; C09K 2211/1029; C09K 2211/1044; H01L 51/0054; H01L 51/0057; H01L 51/0058; H01L 51/5012
See application file for complete search history.

(56) References Cited

U.S. PATENT DOCUMENTS 8,102,116 B2 * 1/2012 Kamatani et al. ............ 313/504
8,431,244 B2 * 4/2013 Ohrui et al. .................. 428/690
(Continued)

FOREIGN PATENT DOCUMENTS

JP    1-289907    11/1989
JP    2-247278    10/1990
(Continued)

OTHER PUBLICATIONS

Allen et al., The Synthesis of Fluoranthene Derivatives, Journal of Organic Chemistry (1952), 17 845-54.
(Continued)

*Primary Examiner* — Dawn L. Garrett
(74) *Attorney, Agent, or Firm* — Cannon U.S.A., Inc. IP Docketing

(57) ABSTRACT

A novel diacenaphtho[1,2-b:1',2'-k]chrysene derivative is provided.

15 Claims, 3 Drawing Sheets

(51) Int. Cl.
  *C09K 11/06* (2006.01)
  *C07C 211/61* (2006.01)
  *C07D 213/06* (2006.01)
  *C07D 239/26* (2006.01)
  *H01L 51/00* (2006.01)
  *H05B 33/14* (2006.01)
  *H01L 51/50* (2006.01)

(52) U.S. Cl.
  CPC ..... *C07C2103/54* (2013.01); *C09K 2211/1011* (2013.01); *C09K 2211/1014* (2013.01); *C09K 2211/1029* (2013.01); *C09K 2211/1044* (2013.01); *H01L 51/5012* (2013.01); *Y10S 428/917* (2013.01)
  USPC ........ 428/690; 252/301.16; 585/27; 428/917; 313/504; 313/506; 257/40

(56) References Cited

U.S. PATENT DOCUMENTS

| | | | |
|---|---|---|---|
| 8,431,711 | B2 | 4/2013 | Kamatani et al. |
| 8,519,613 | B2* | 8/2013 | Kamatani et al. ............. 313/504 |
| 2004/0076853 | A1* | 4/2004 | Jarikov ........................ 428/690 |
| 2004/0150328 | A1 | 8/2004 | Czerw |
| 2008/0007157 | A1 | 1/2008 | Carroll |
| 2010/0157131 | A1 | 6/2010 | Kamatani et al. |
| 2013/0216268 | A1 | 8/2013 | Kamatani et al. |

FOREIGN PATENT DOCUMENTS

| | | |
|---|---|---|
| JP | 8-113576 | 5/1996 |
| JP | 10-294177 | 11/1998 |
| JP | 11-12205 | 1/1999 |
| JP | 2000-505821 | 5/2000 |
| JP | 2000-186054 | 7/2000 |
| JP | 2001-102173 | 4/2001 |
| WO | 2007/139345 A | 12/2007 |
| WO | 2007/139345 A1 | 12/2007 |
| WO | 2008-120806 | 10/2008 |

OTHER PUBLICATIONS

Montoya-Pelaez et al., The Synthesis and Resolution of 2,2prime-, 4,4prime-, and 6,6prime-Substituted Chiral Biphenyl Derivatives for Application in the Preparation of Chiral Materials, J. Org. Chem. 2006, 71, 5921-5929.

Wegner et al., A New Suzuki-Heck-Type Coupling Cascade: Indeno[1,2,3]-Annelation of Polycyclic Aromatic Hydrocarbons, J. Org. Chem. 2003, 68, 883-887.

Coventry et al., Selective Ir-catalysed borylation of polycyclic aromatic hydrocarbons: structures of naphthalene-2, 6-bis(boronates), pyrene-2, 7-bis(boronate) an perylene-2, 5, 8, 11-tetra(boronate) esters, Chem. Commun., 2005, 2172-2174.

* cited by examiner

DIACENAPHTHO[1,2-B:1',2'-K]CHRYSENE DERIVATIVE

TECHNICAL FIELD

The present invention relates to diacenaphtho[1,2-b:1',2'-k]chrysene derivative having a novel backbone.

BACKGROUND ART

An organic light-emitting device includes an anode, a cathode, and a thin film that contains a fluorescent organic compound and is interposed between the anode and the cathode. When electrons and holes are injected from the respective electrodes, excitons of the fluorescent compound are generated and the light emitted by the excitons returning to their ground state is utilized by the device.

Recent advancement of organic light-emitting devices has been remarkable and suggested possibilities of applying the devices to a wider range of usages. This is because they can achieve high luminance with low voltage, a wider range of emission wavelengths, rapid response, and reduction in thickness and weight.

However, under existing conditions, further improvements are needed in terms of luminance of the optical output and conversion efficiency. Moreover, many problems on durability remain such as changes over time resulting from long-time uses and deterioration caused by oxygen-containing atmosphere gas and humidity.

In order for devices to be applicable to full-color displays and the like, emission efficiency and the color purity must be high. However, this is not yet achieved. Organic light-emitting devices that achieve high color purity, high emission efficiency, and high durability and materials that can realize such organic light-emitting devices are desired.

Although Patent Citations 1 to 4 disclose materials for emission layers that achieve higher emission efficiency, none of these materials is sufficient for practical application. Development of new materials that achieve high quantum yield is desired.

Patent Citation 1
Japanese Patent Laid-Open No. 1-289907
Patent Citation 2
Japanese Patent Laid-Open No. 2-247278
Patent Citation 3
Japanese Patent Laid-Open No. 8-113576
Patent Citation 4
Japanese Patent Laid-Open No. 11-12205

DISCLOSURE OF INVENTION

Technical Problem

The organic compounds and the organic light-emitting devices that contain the organic compounds described in Patent Citations above have a room for improvements from the practical viewpoint.

To be more specific, optical output that achieves ever higher luminance and conversion efficiency is needed for practical application. Moreover, improvements on durability such as changes over time caused by long-time uses and deterioration caused by humidity and oxygen-containing atmosphere gas are needed.

In order for organic light-emitting devices to be applicable to full-color displays and the like, they must achieve blue emission at high color purity and high efficiency, but this has not been satisfactorily achieved.

Organic light-emitting devices that achieve high color purity, high emission efficiency, and high durability and materials that can realize such organic light-emitting devices are desired.

Solution to Problem

It is desirable to provide a novel organic compound suitable for use in blue light-emitting devices. The inventors of the present invention have conducted extensive studies and made the present invention.

An aspect of the present invention provides a diacenaphtho [1,2-b:1',2'-k]chrysene derivative having a backbone represented by the following formula:

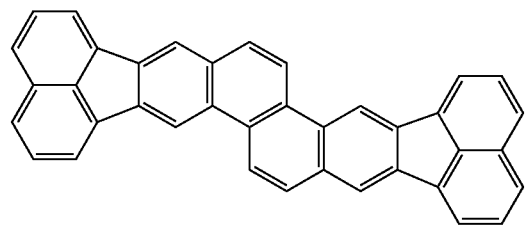 [SMILES: c1cc2c3c(cccc3c1)-c1cc3c(ccc4c5cc6c(cc5ccc34)-c3cccc4cccc-6c34)cc1-2]

Advantageous Effects of Invention

A diacenaphtho[1,2-b:1,2'-k]chrysene derivative of the present invention has high-efficiency, high-luminance emission performance. An organic light-emitting device containing this compound can achieve high luminance emission at high efficiency and high durability.

DESCRIPTION OF EMBODIMENTS

Figure 1:
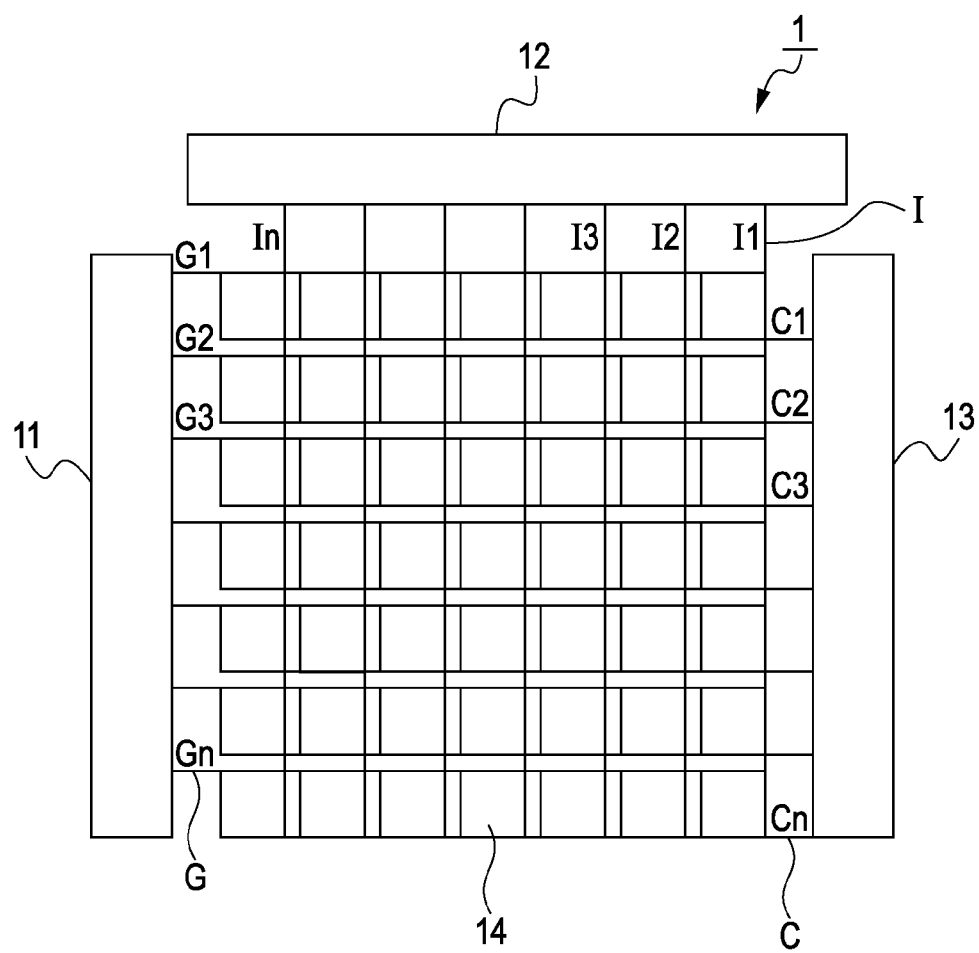
FIG. 1 is a schematic diagram illustrating an organic light-emitting device according to one embodiment and a unit configured to supply electrical signals to the organic light-emitting device.

Compounds of the present invention will now be described in details.

The backbone of diacenaphtho[1,2-b:1',2'-k]chrysene derivatives of the present invention is novel.

The backbone of the diacenaphtho[1,2-b:1',2'-k]chrysene derivatives is represented below:

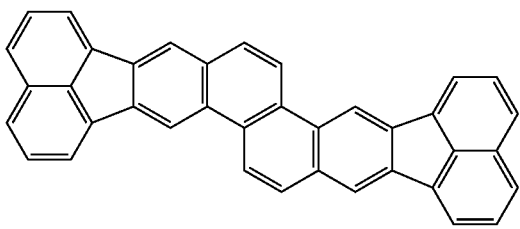 [SMILES: c1cc2c3c(cccc3c1)-c1cc3c(ccc4c5cc6c(cc5ccc34)-c3cccc4cccc-6c34)cc1-2]

In particular, the diacenaphtho[1,2-b:1',2'-k]chrysene derivatives of the present invention are represented by general formula (1) below:

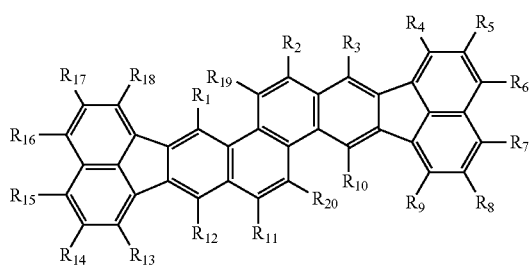

(I)

$R_1$ to $R_{20}$ each independently represent a hydrogen atom, a halogen atom, a substituted or unsubstituted alkyl group, a substituted or unsubstituted alkoxy group, a substituted or unsubstituted amino group, a substituted or unsubstituted aryl group, or a substituted or unsubstituted heterocyclic group.

Specific examples of the substituents in the compounds represented by general formula (1) are as follows.

In formula (1), examples of the alkyl group in the substituted or unsubstituted alkyl group include, but are not limited to, a methyl group, an ethyl group, a normal propyl group, an iso-propyl group, a normal butyl group, a tert-butyl group, a sec-butyl group, an octyl group, a 1-adamantyl group, and a 2-adamantyl group.

In formula (1), examples of the alkoxy group in the substituted or unsubstituted alkoxy group include, but are not limited to, a methoxy group, an ethoxy group, a propoxy group, a 2-ethyl-octyloxy group, a phenoxy group, a 4-tert-butylphenoxy group, a benzyloxy group, and a thienyloxy group.

In formula (1), examples of the amino group in the substituted or unsubstituted amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

In formula (1), examples of the aryl group in the substituted or unsubstituted aryl group include, but are not limited to, a phenyl group, a naphthyl group, an indenyl group, a biphenyl group, a terphenyl group, and a fluorenyl group.

In formula (1), examples of the heterocyclic group in the substituted or unsubstituted heterocyclic group include, but are not limited to, a pyridyl group, an oxazolyl group, an oxadiazolyl group, a thiazolyl group, a thiadiazolyl group, a carbazolyl group, an acridinyl group, and a phenanthrolyl group.

In formula (1), examples of the substituent that may be included in the above-described substituents, namely, the alkyl, alkoxy, amino, aryl, and heterocyclic groups, include, but are not limited to, alkyl groups such as a methyl group, an ethyl group, and a propyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, a propoxyl group, and a phenoxyl group; a cyano group; and halogen atoms such as fluorine, chlorine, bromine, and iodine atoms.

Specific non-limiting examples of the compound represented by general formula (1) are as follows:

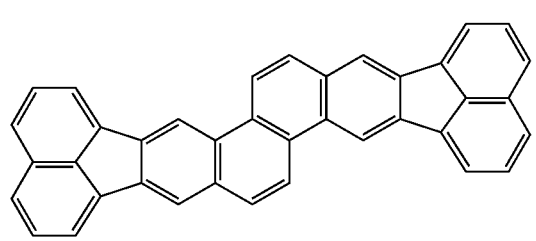

A1

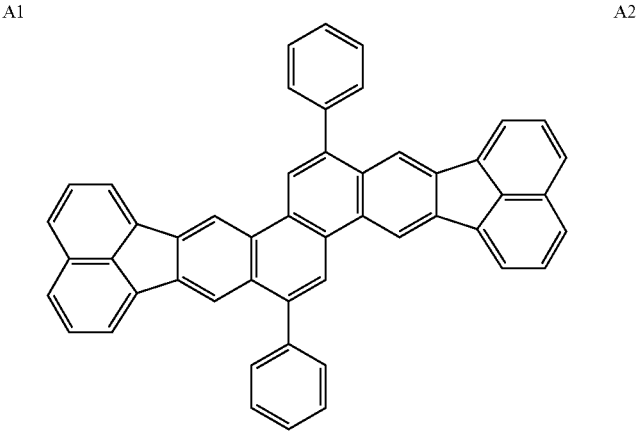

A2

-continued
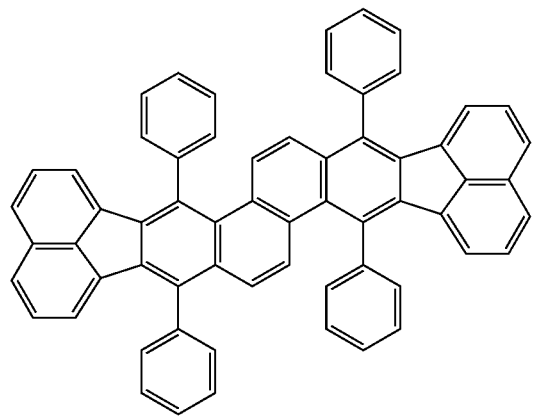
A3
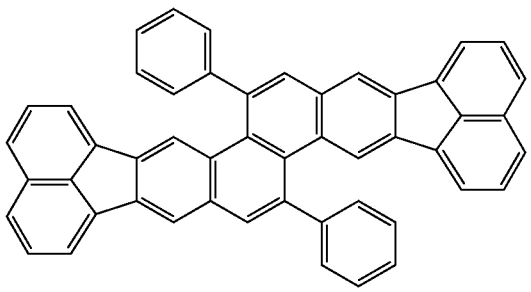
A4
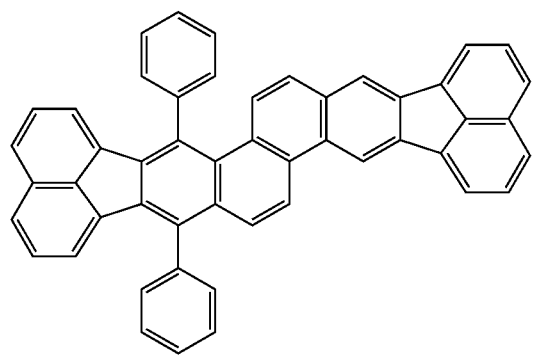
A5
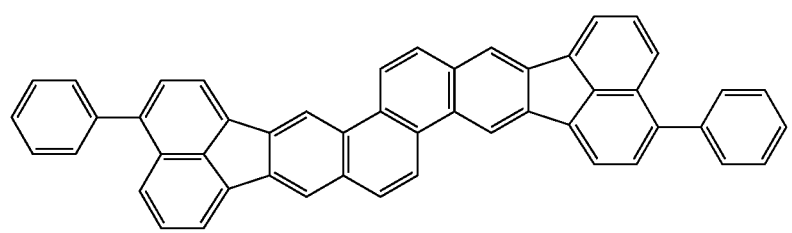
A6
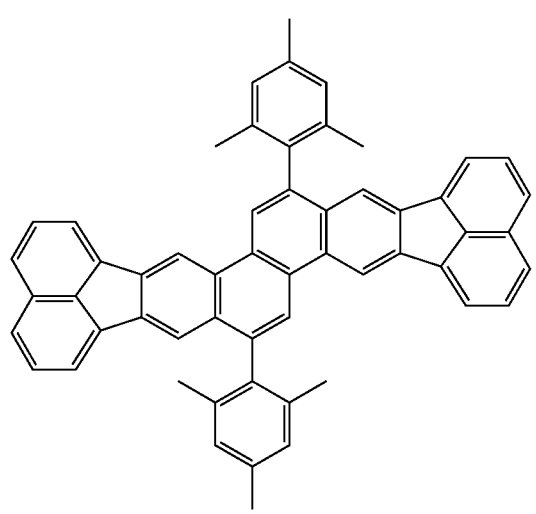
A7
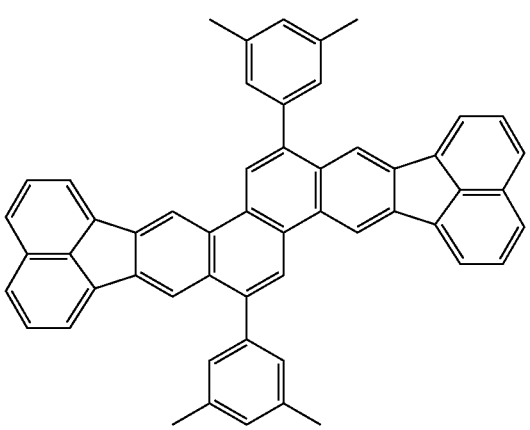
A8

-continued
A9
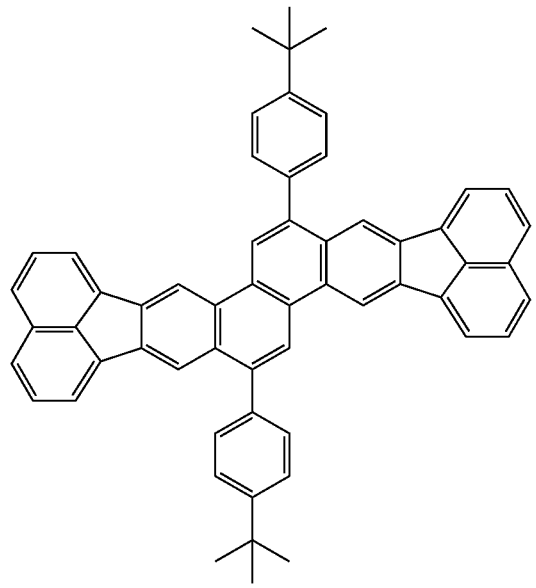
A10
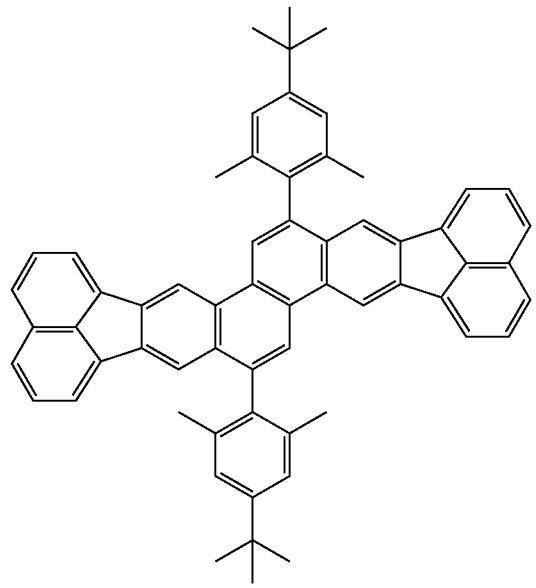
A11
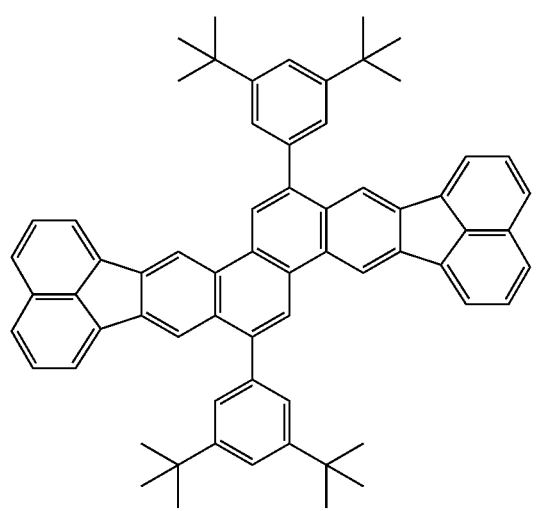
A12
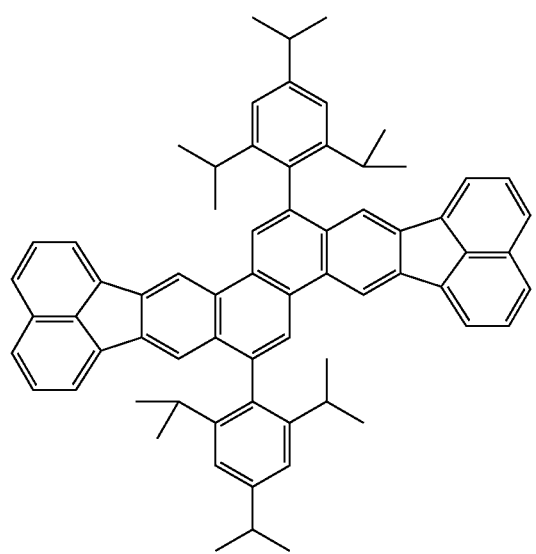
A13
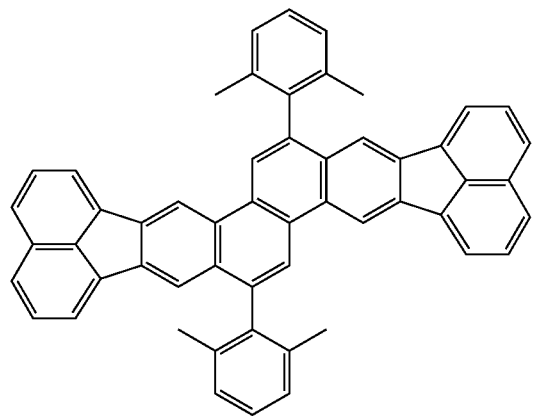
A14
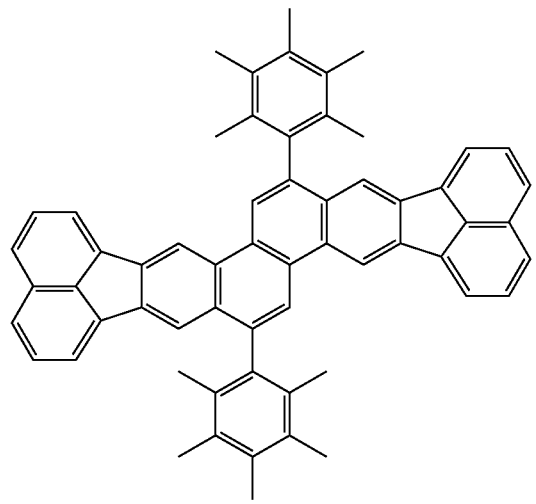

-continued
A15
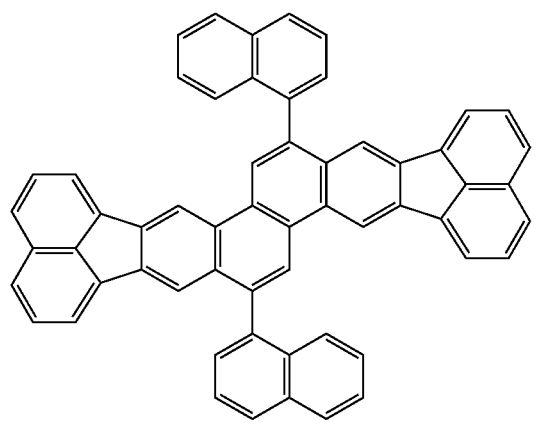
A16
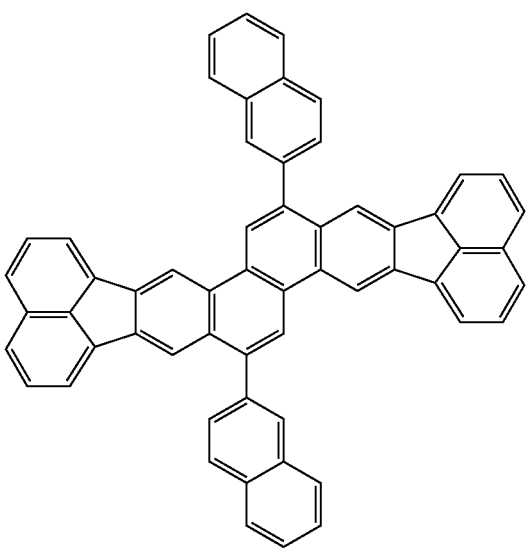
A17
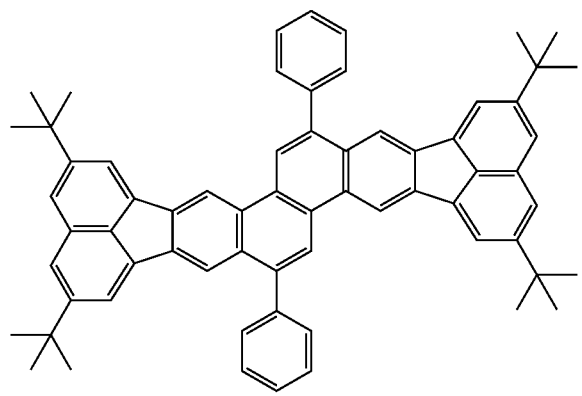
A18
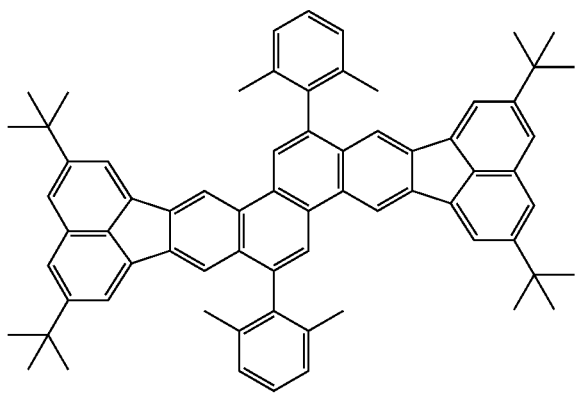
A19
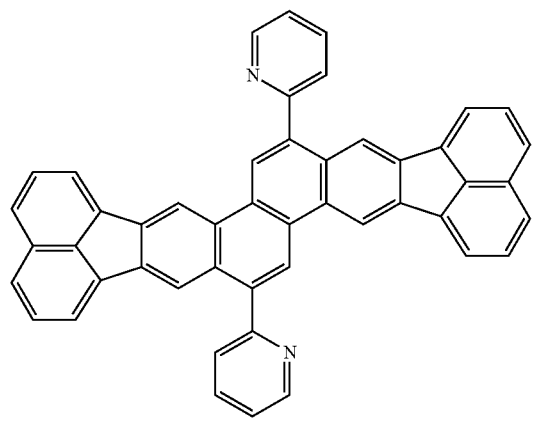
A20
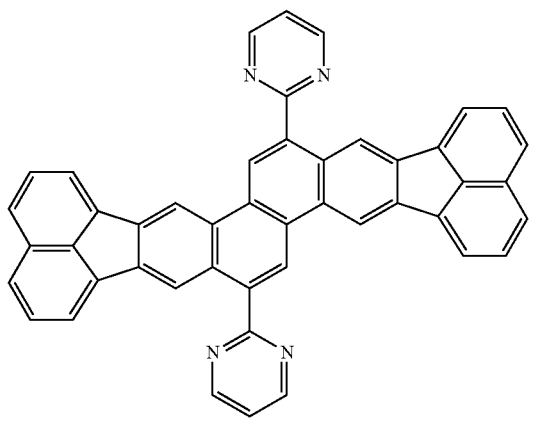

-continued
A21
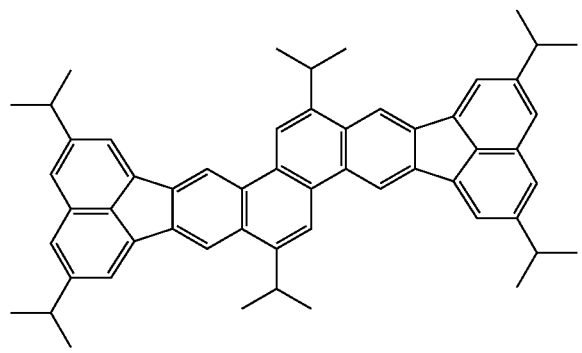
A22
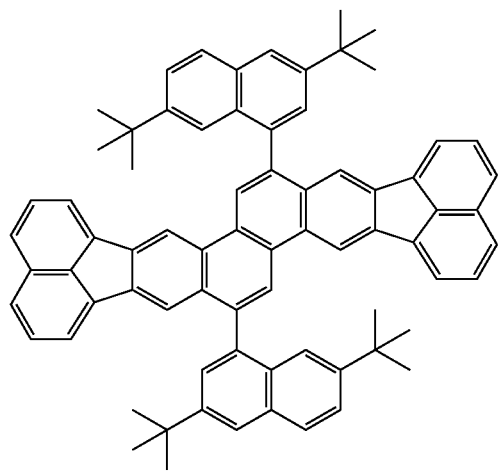
A23
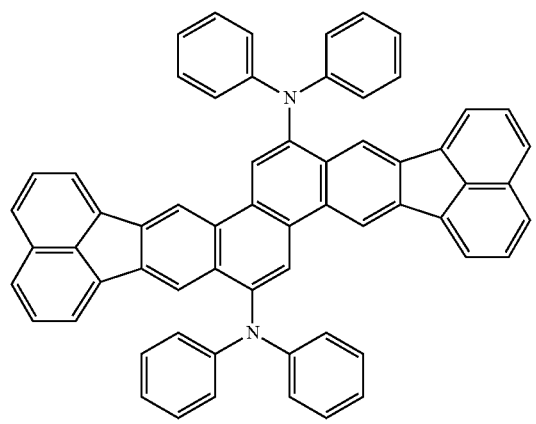
A24
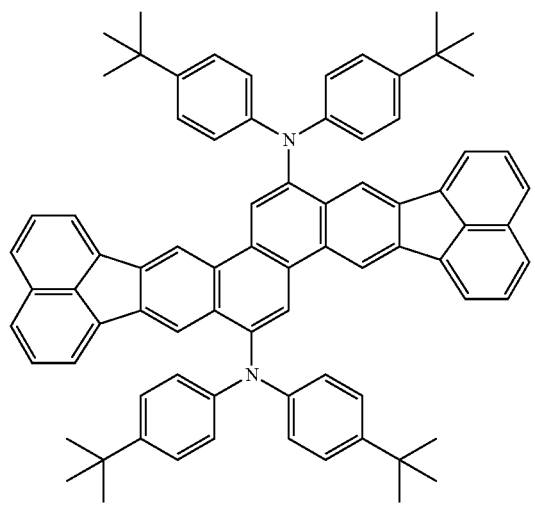
A25
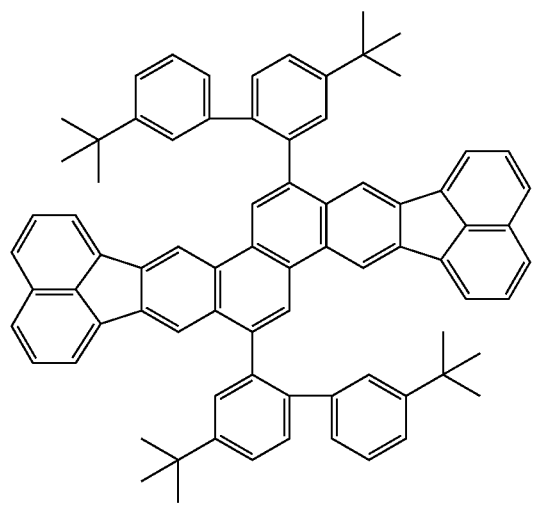
A26
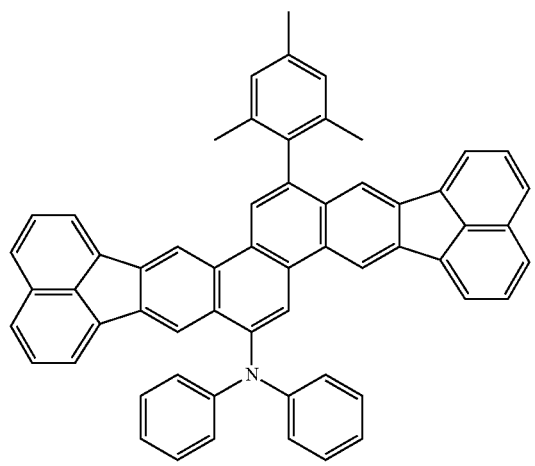

-continued
A27
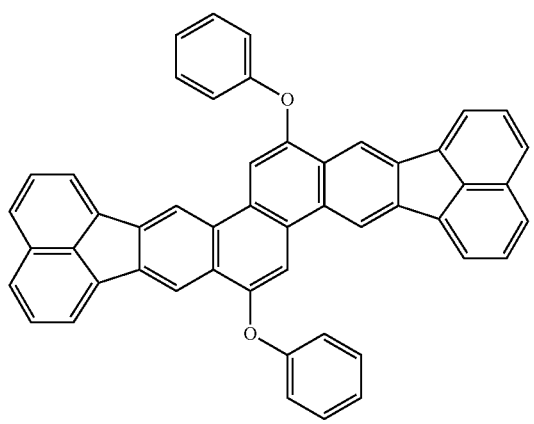
A28
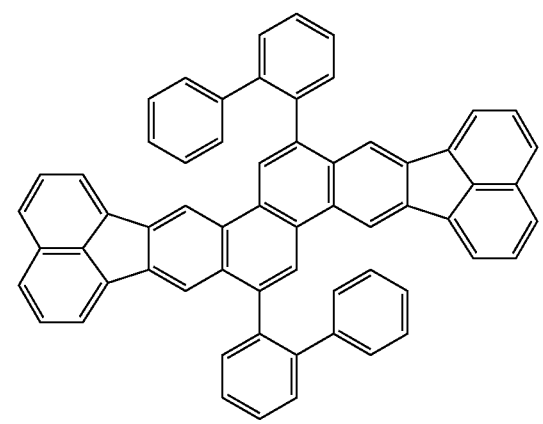
A29
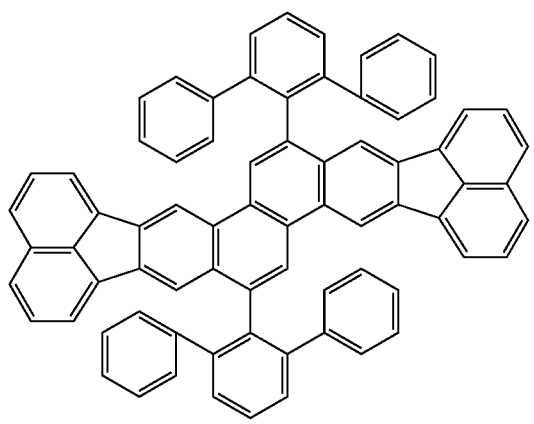
A30
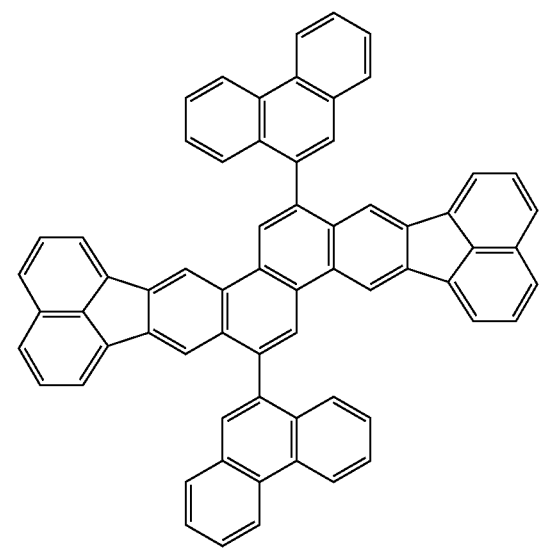
A31
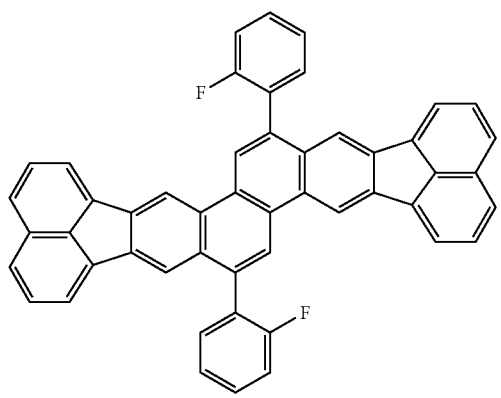
A32
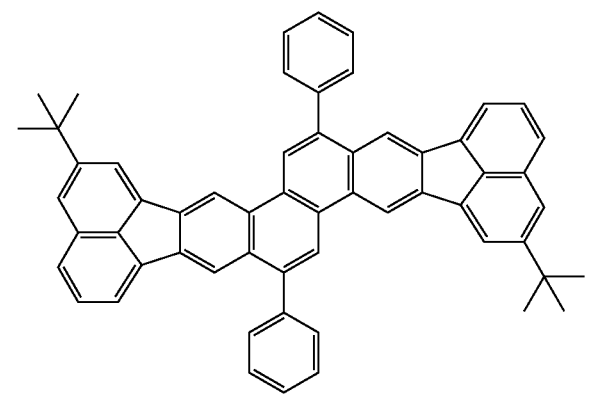

-continued
A33
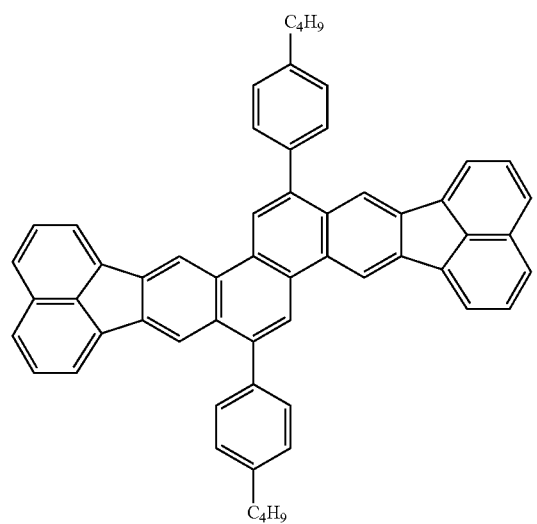
A34
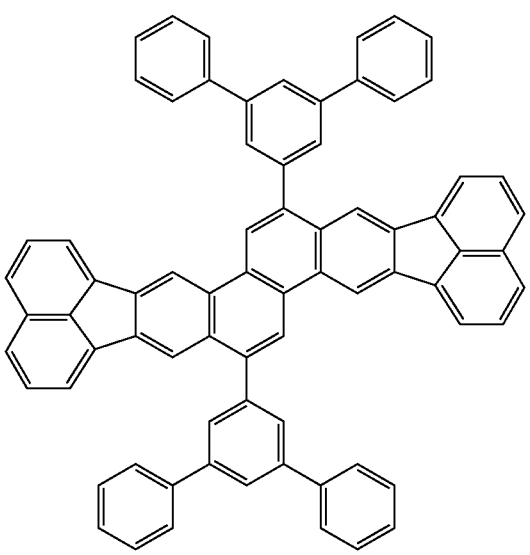
A35
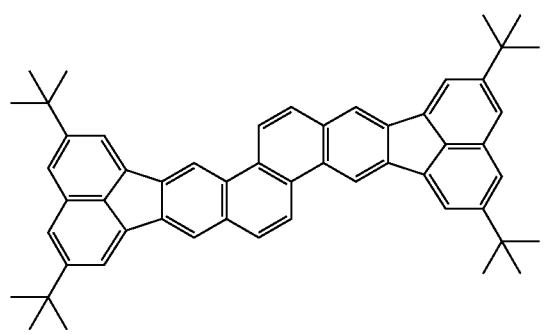
A36
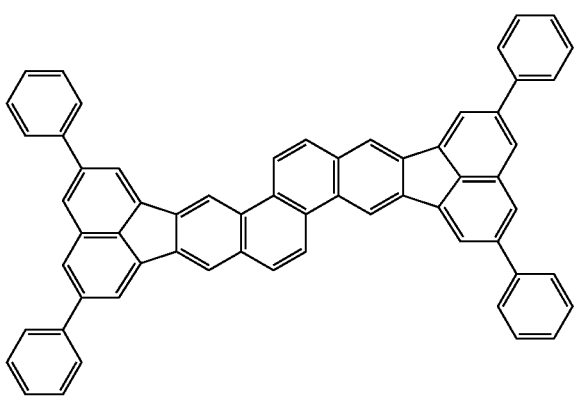
A37
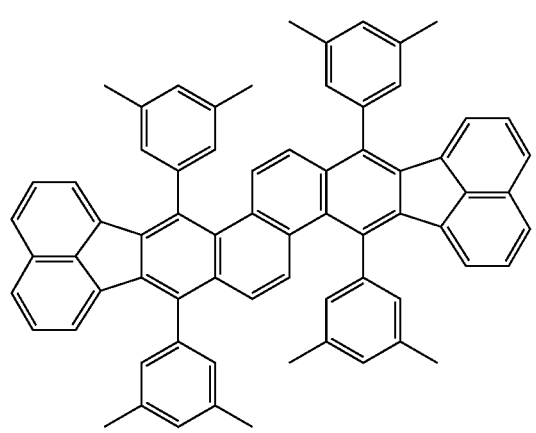
A38
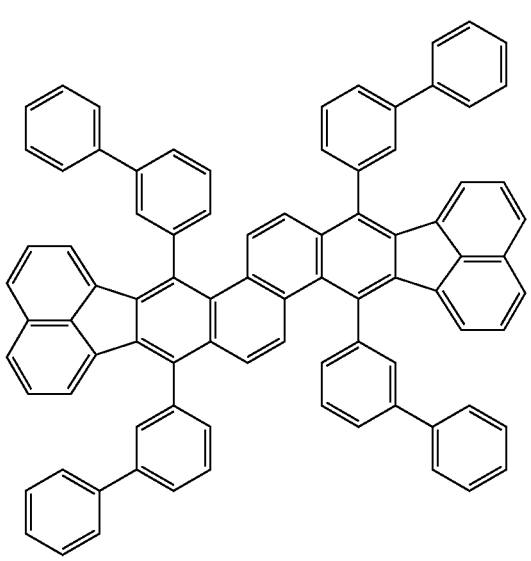

-continued
A39
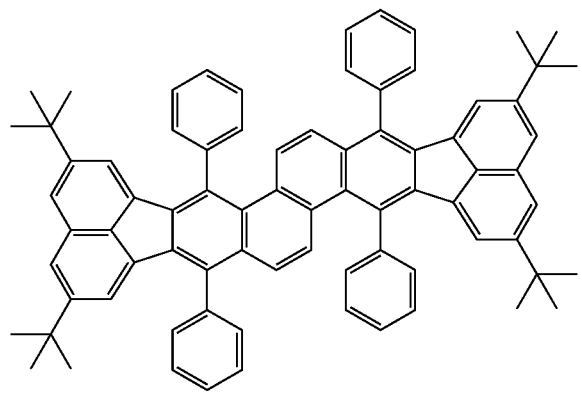
A40
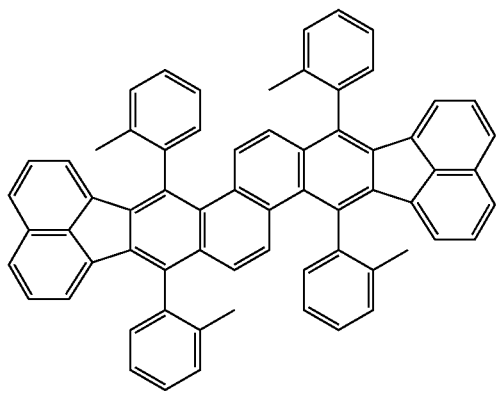
A41
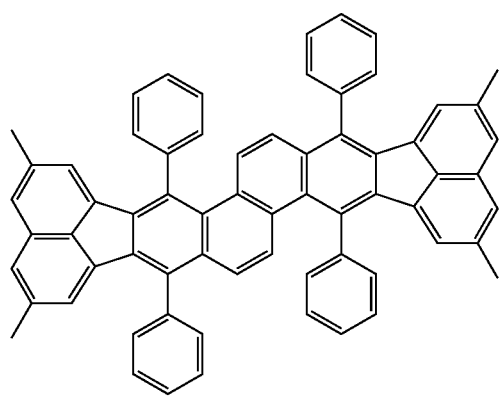
A42
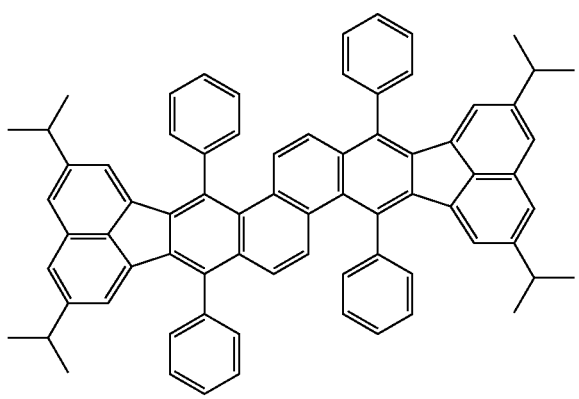
A43
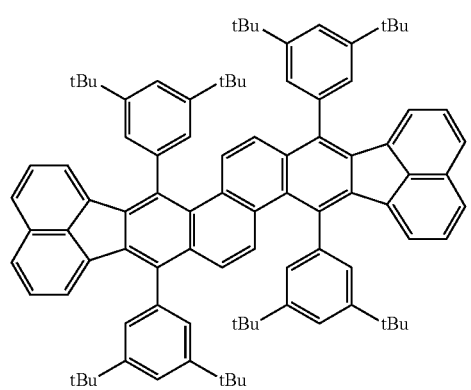
A44
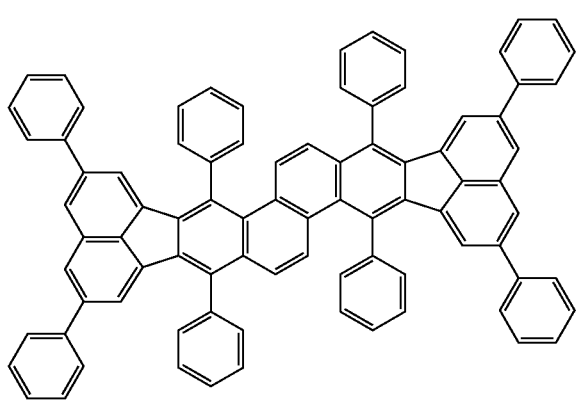
A45
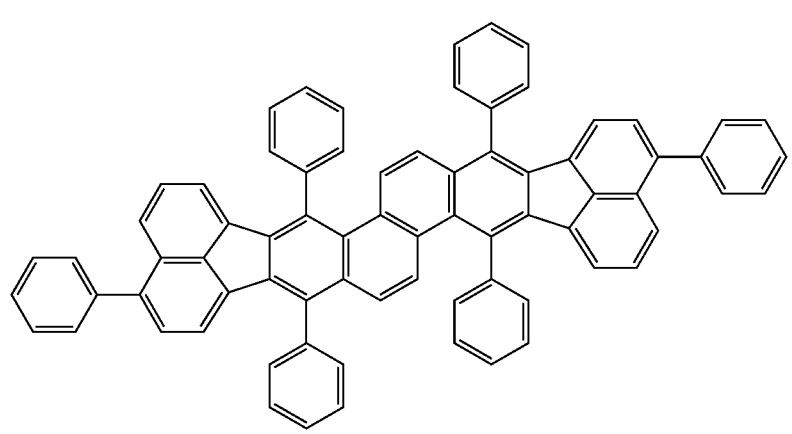

-continued
A46
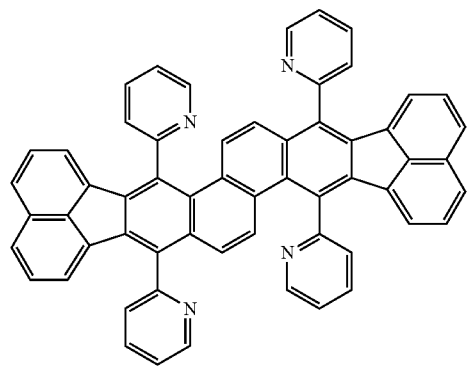
A47
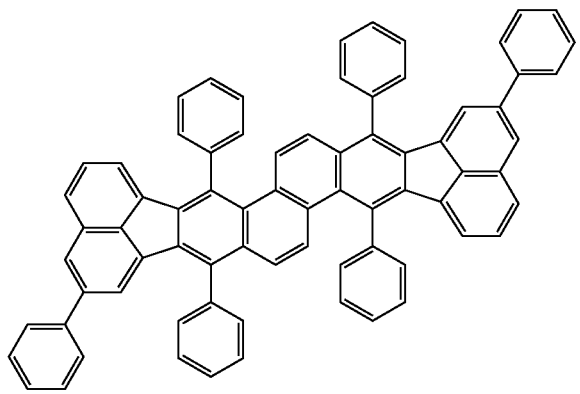
A48
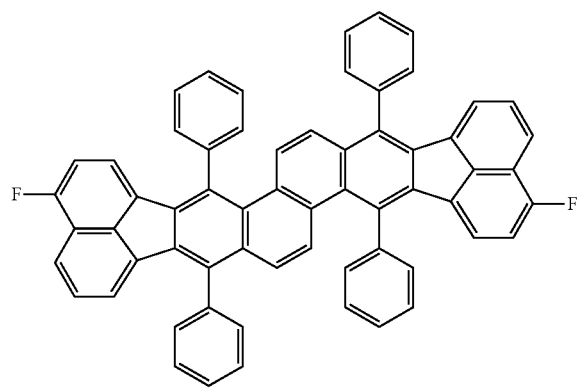
A49
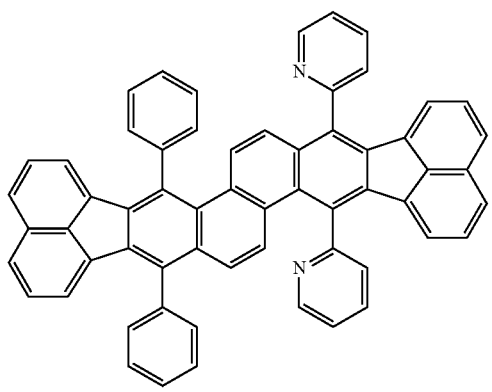
A50
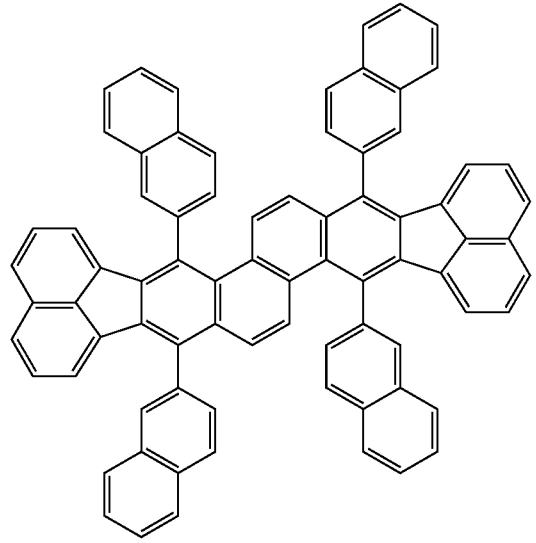
A51
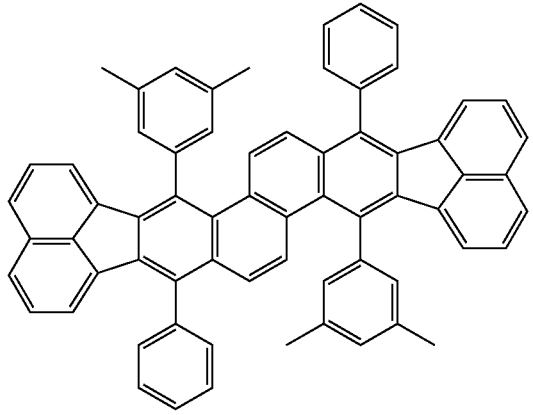

-continued
A52
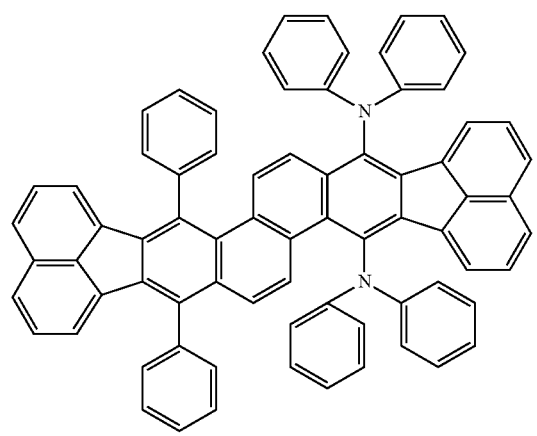
A53
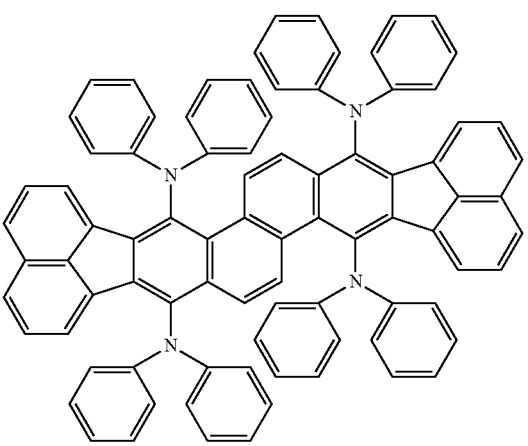
A54
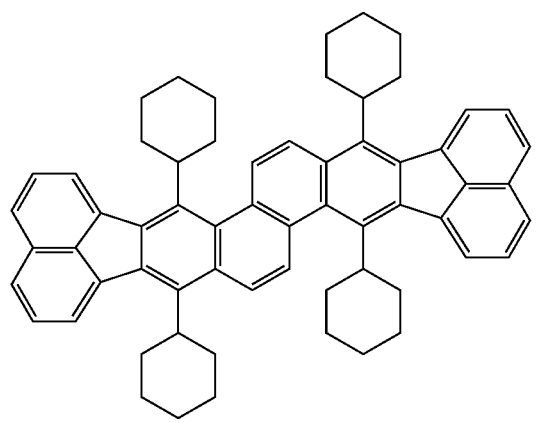
A55
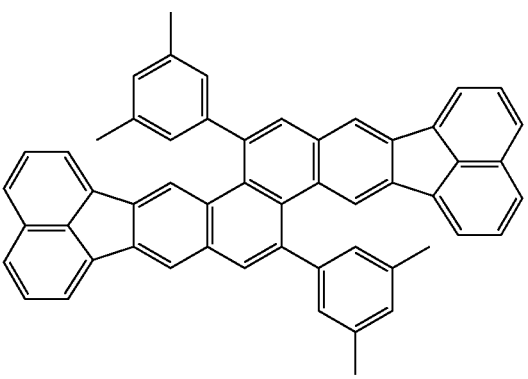
A56
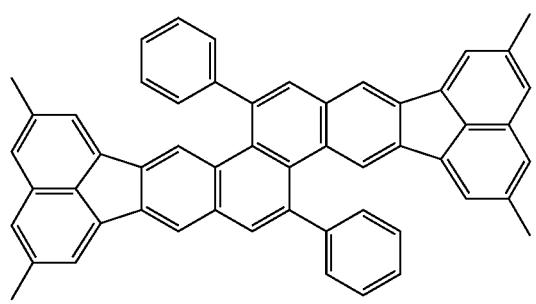
A57
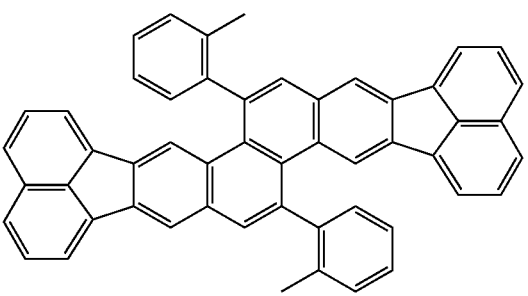
A58
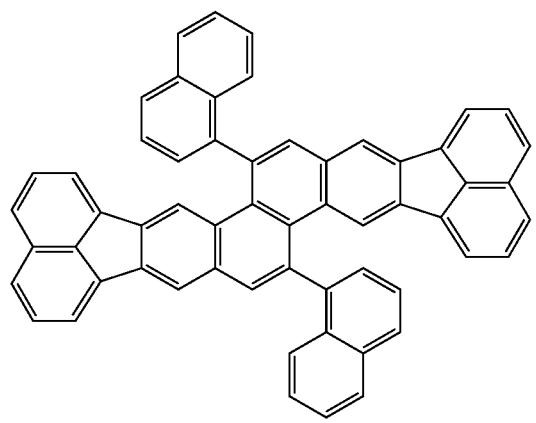
A59
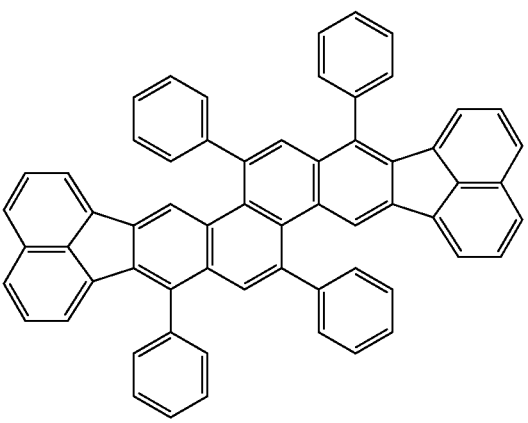

-continued
A60
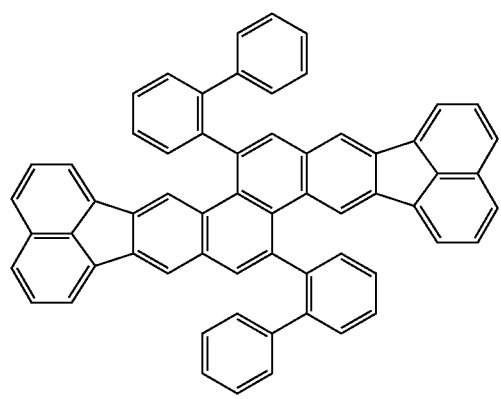
A61
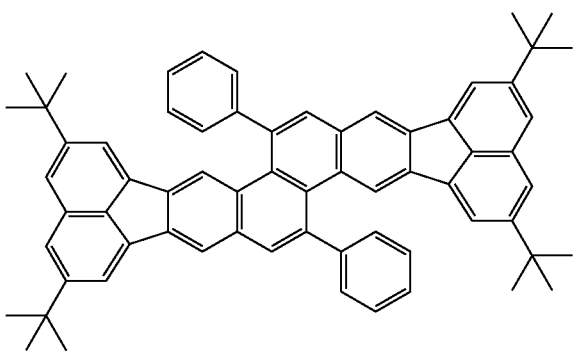
A62
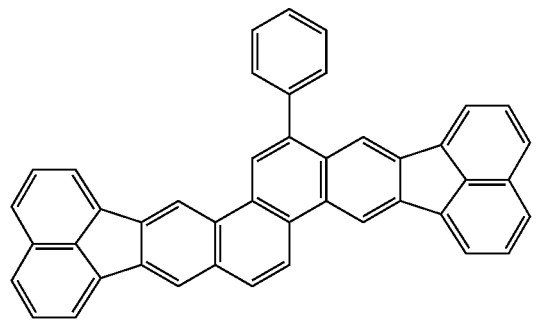
A63
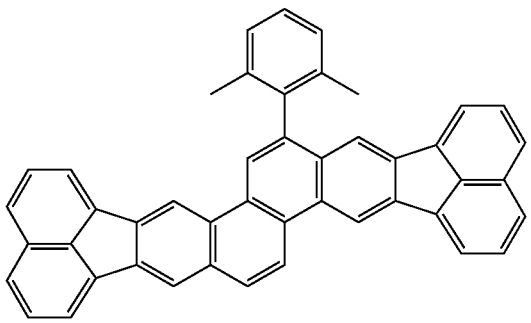
A64
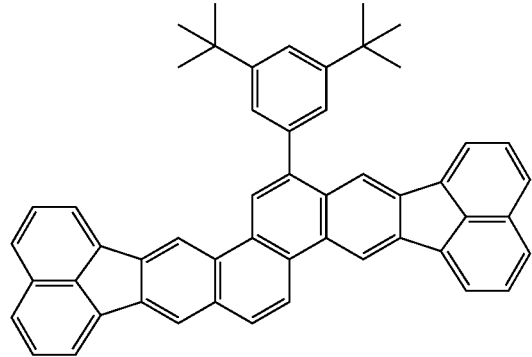
A65
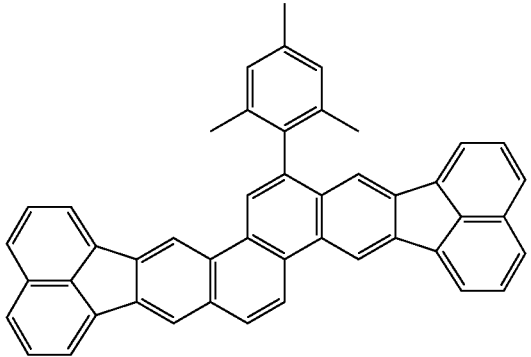
A66
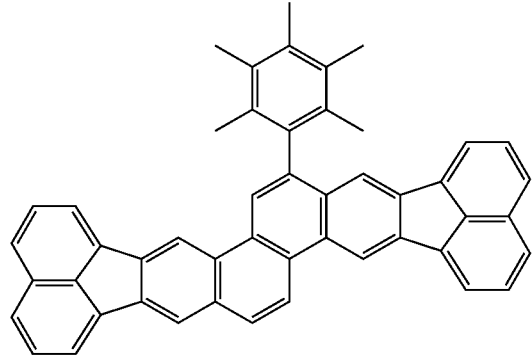
A67
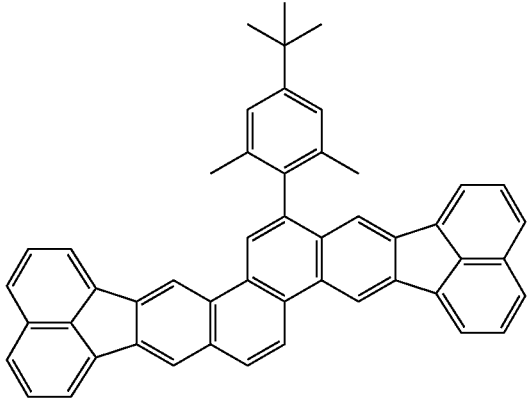

-continued
A68
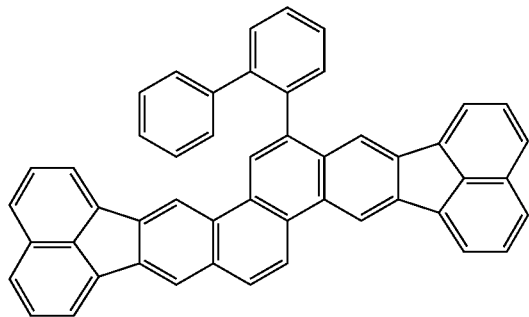
A69
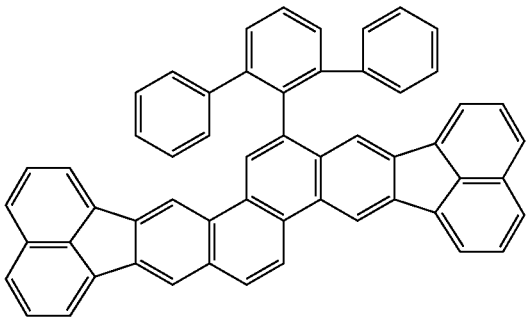
A70
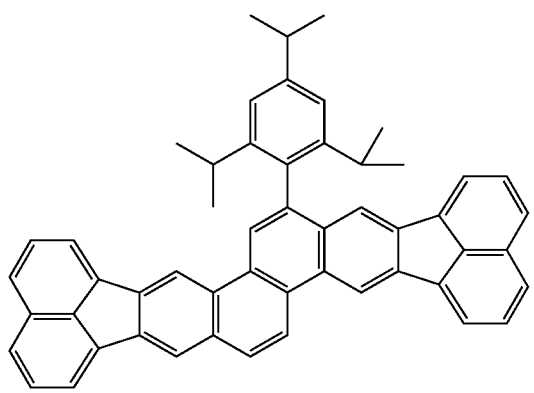
A71
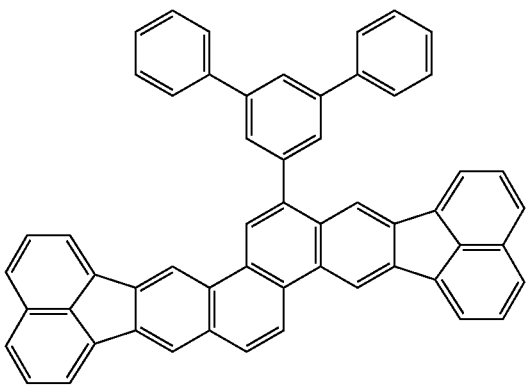
A72
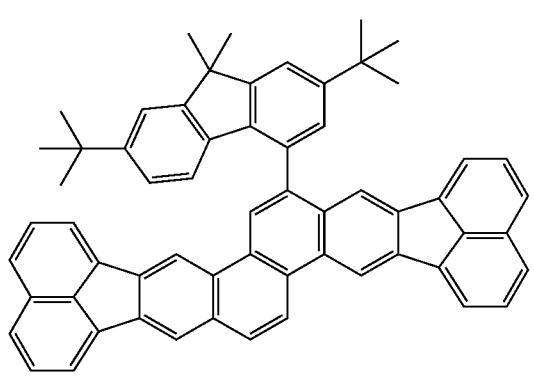
A73
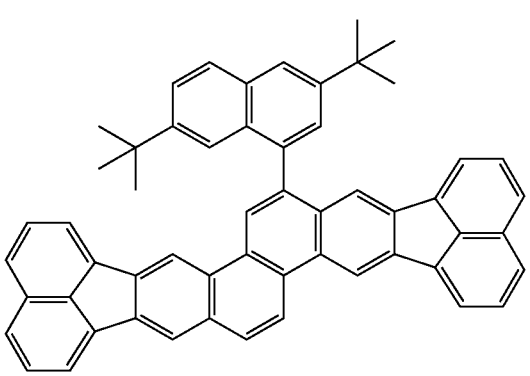
A74
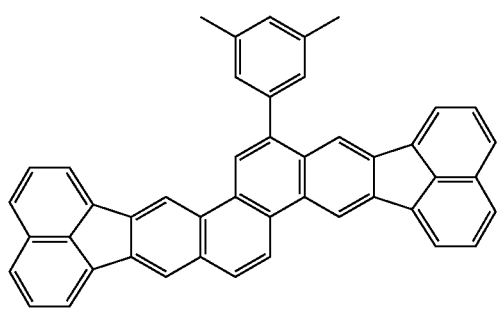
A75
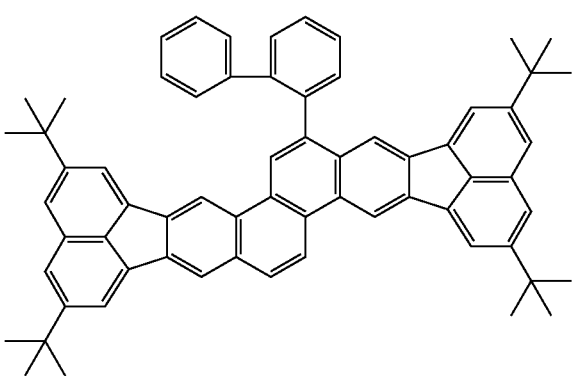

-continued
A76
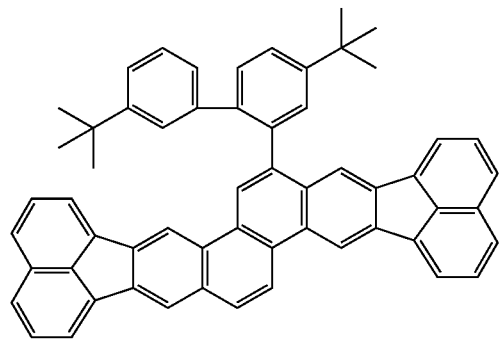
A77
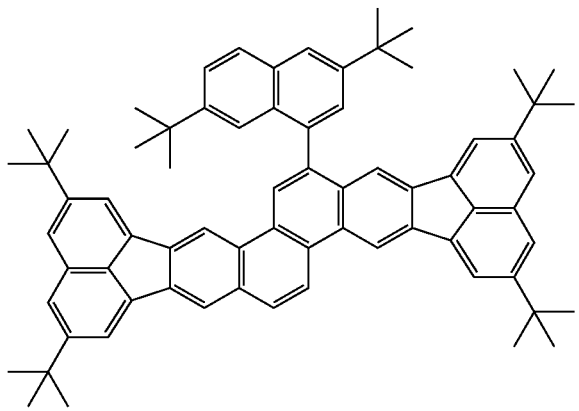
A78
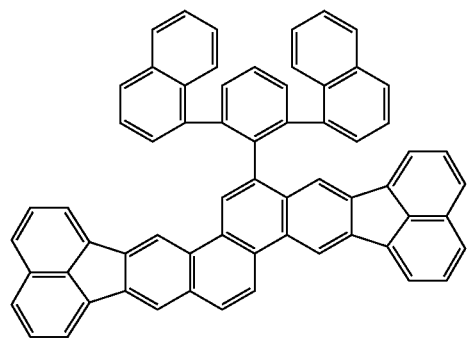
A79
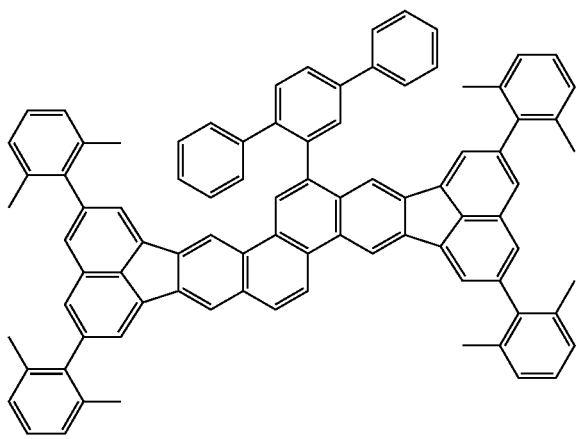
A80
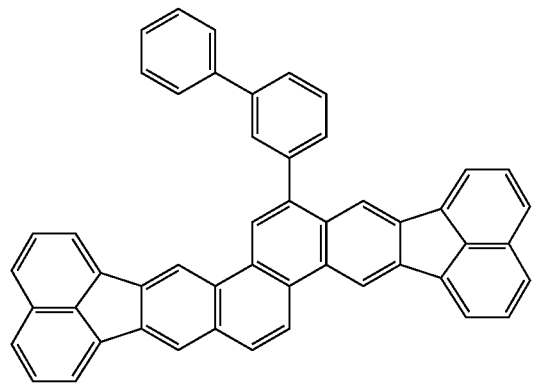
A81
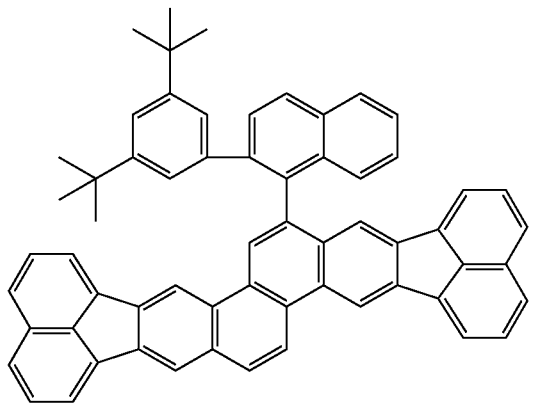
A82
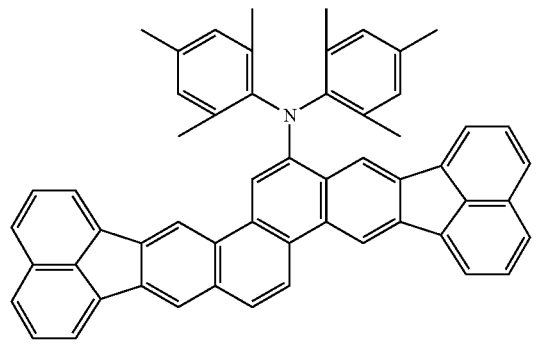
A83
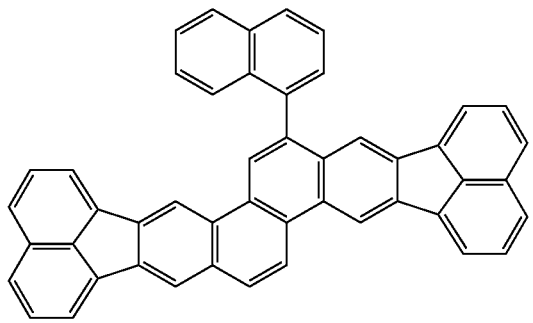

-continued
A84
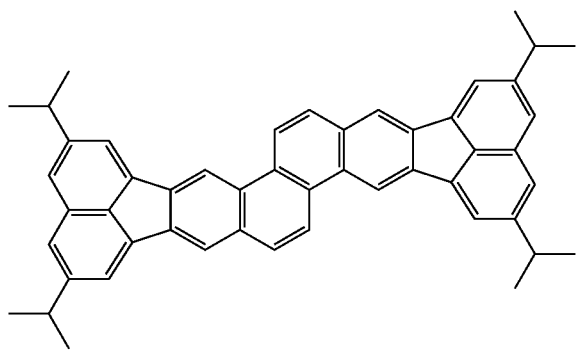
A86
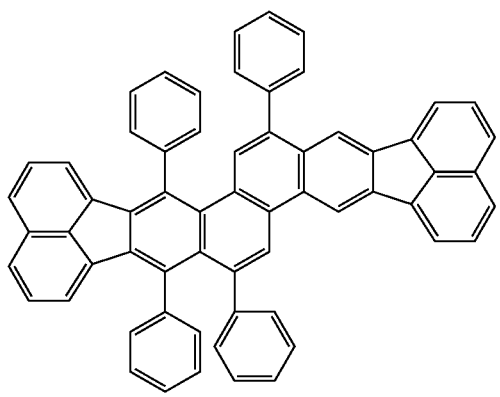
A87
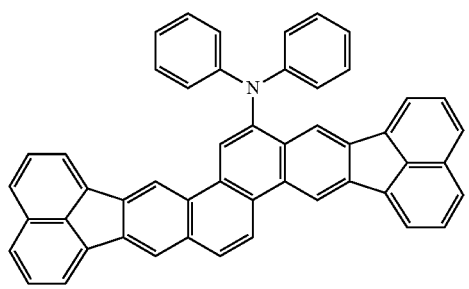
A88
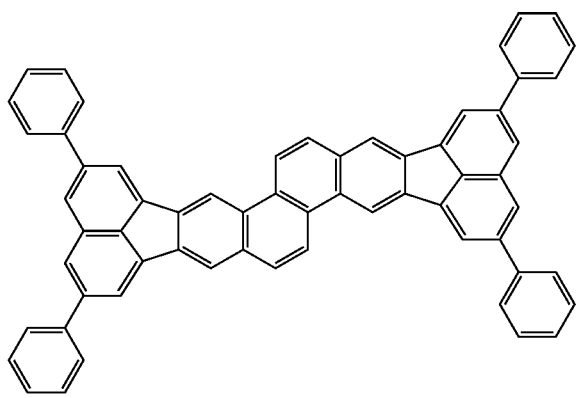
A89
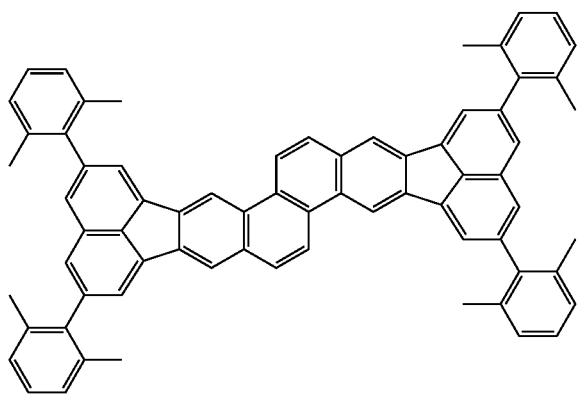
A90
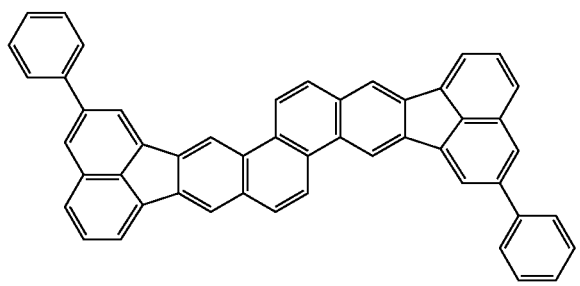
A91
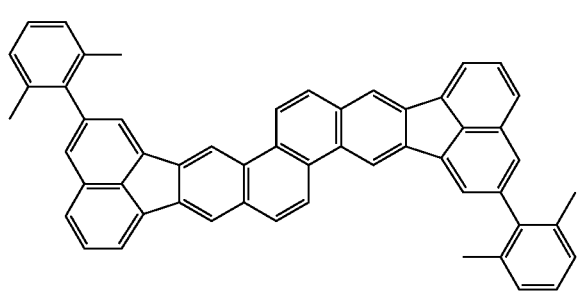

The compound of the present invention will now be described in further detail.

In general, in order to increase the emission efficiency of organic light-emitting devices, the emission quantum yield of the emission center material itself is desirably high.

The studies conducted by the inventors have found that the compounds represented by general formula (1) exhibit a high quantum yield in diluted solutions. A high emission efficiency can be expected by using a compound represented by general formula (1) in an organic light-emitting device.

The organic compound of the present invention is a derivative having a diacenaphtho[1,2-b:1',2'-k]chrysene backbone.

In using an organic compound as a light-emitting material, it is essential that the material itself have a high quantum yield. This requires, first, that the oscillator strength be high and, second, that the oscillating portion of the backbone associated with emission be small. The inventors consider it critical that both these conditions be met.

With respect to the first condition, it is important to enhance the symmetry of the backbone associated with emission from molecules. However, no emission would occur under a forbidden transition condition peculiar to highly symmetrical molecules. The oscillator strength improves as a result of an increased moment of the molecules when the conjugation is extended in the same direction.

With respect to the second condition, the decrease in quantum yield resulting from oscillation caused by rotation can be suppressed when the backbone associated with emission is free of any rotational structure.

Figure 5:
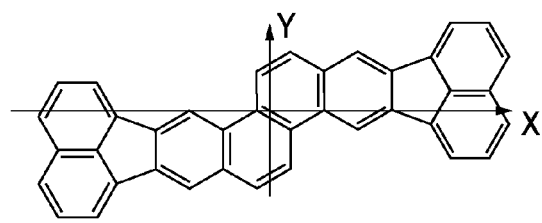
FIG. 5 shows the backbone of diacenaphtho[1,2-b:1',2'-k]chrysene derivatives and the X axis and the Y axis indicating the moment.

FIG. 5 shows the backbone of diacenaphtho[1,2-b:1',2'-k]chrysene derivatives of the present invention and the X axis and the Y axis perpendicular to the X axis for explaining the moment.

Referring to FIG. 5, as for the first condition, the backbone can be considered to have a high oscillator strength since the moment in the X axis direction is large. The backbone also has good symmetry. As for the second condition, since there is no rotational axis in the backbone, a decrease in quantum yield caused by vibrational deactivation does not occur. Thus the backbone is suitable for light-emitting materials.

Diacenaphtho[1,2-b:1',2'-k]chrysene derivatives have a high planarity and easily generate excimers when they are not substituted. To prevent generation of excimers, a substituent can be introduced. The position into which the substituent is introduced is not particularly limited but the 7-, 9-, 10-, 17-, 19-, and 20-positions that are close to the center of the backbone are suitable.

The formula below shows the numbers of the substitution sites in the backbone of the diacenaphtho[1,2-b:1',2'-k]chrysene derivatives:

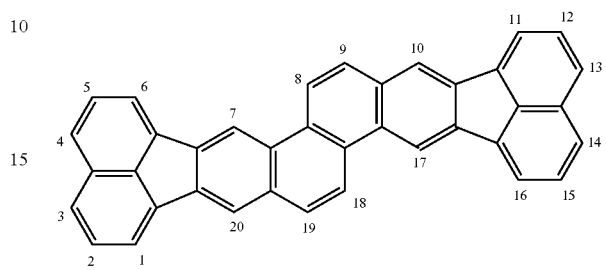

As described above, the diacenaphtho[1,2-b:1',2'-k]chrysene derivatives of the present invention feature that their backbone has a high oscillator strength and contains a smaller amount of oscillating portions associated with emission.

Moreover, the backbone of the diacenaphtho[1,2-b:1',2'-k]chrysene derivatives is novel. The inventors believe that these properties contribute to achieving highly efficient emission performance and high luminance.

Note that the diacenaphtho[1,2-b:1',2'-k]chrysene derivatives represented by general formula (1) can be synthesized by following synthetic routes 1 to 4 with reference to J. Org. Chem. 1952, 17, 845-54, J. Org. Chem. 2006, 71, 5921-5929, J. Org. Chem. 2003, 68, 883-887, and Chem. Commun., 2005, 2172-2174, for example. A substituent may be introduced into the backbone of the diacenaphtho[1,2-b:1',2'-k]chrysene derivatives by, for example, substituting a hydrogen atom with a substituent such as an alkyl group, a halogen atom, a phenyl group, or the like in the synthesis.

Synthetic Route 1

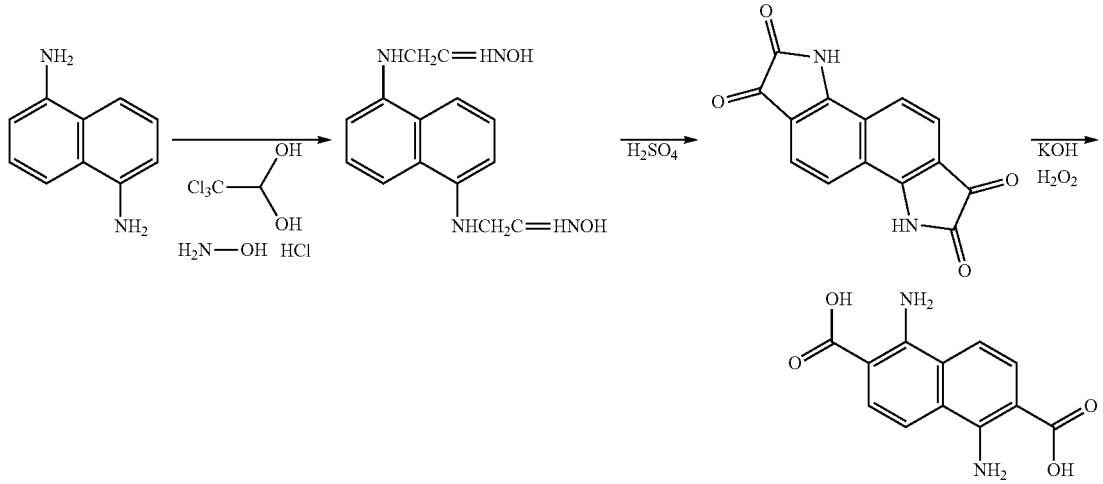

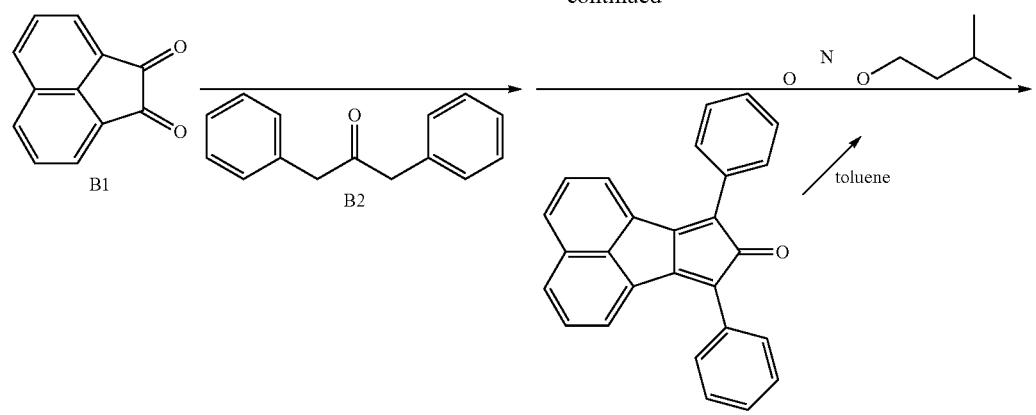
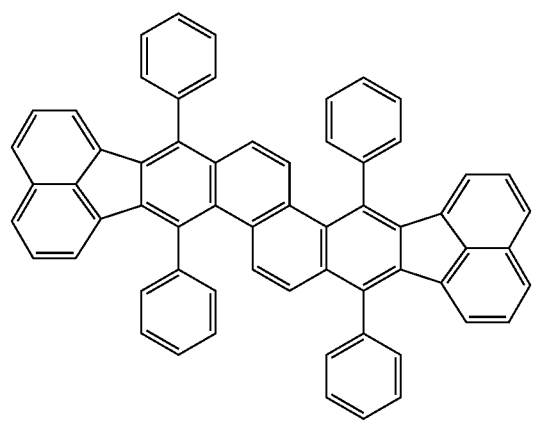
Synthetic Route 2
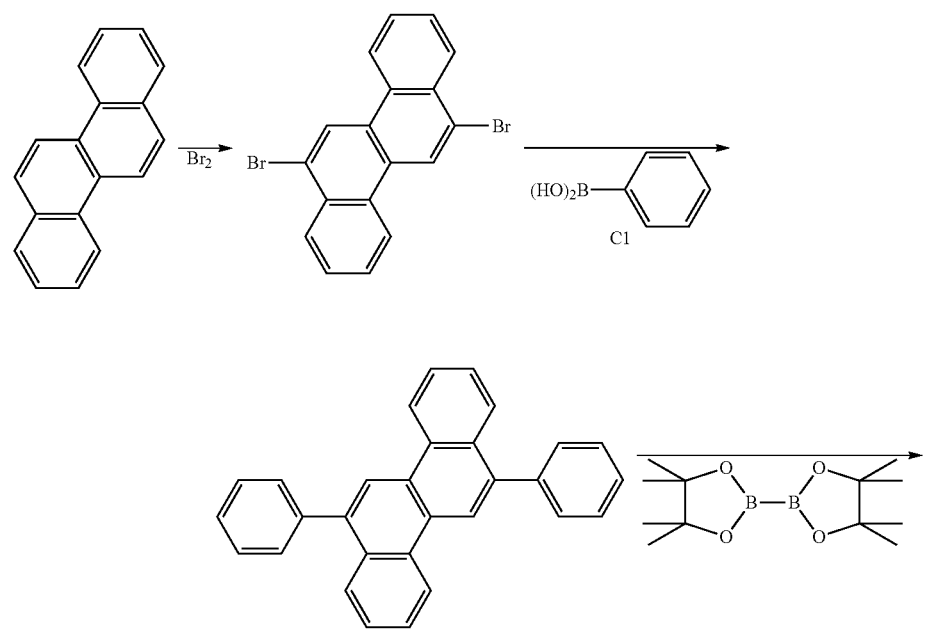

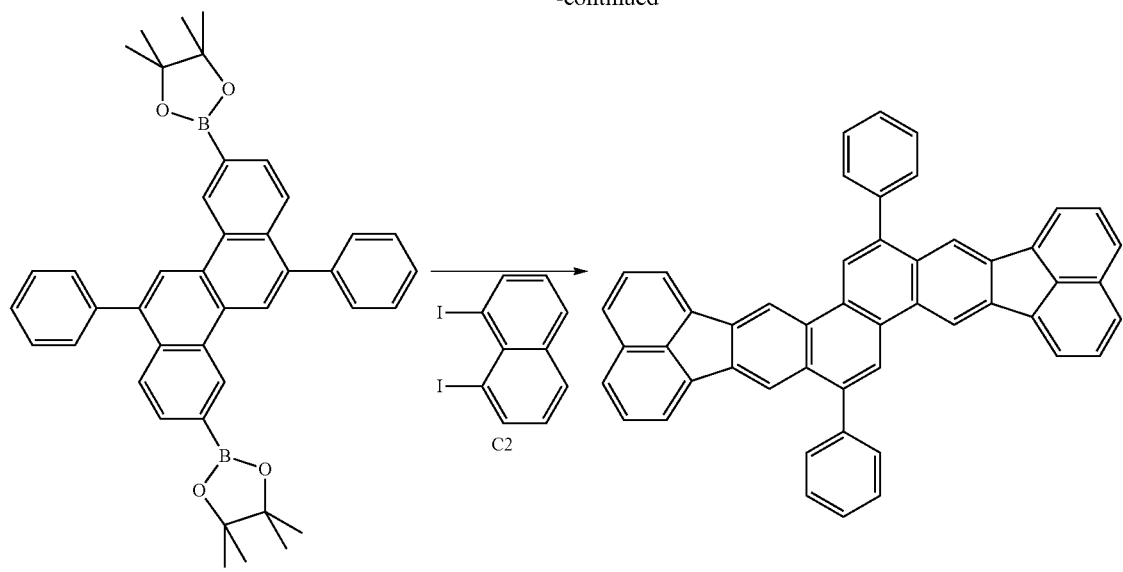
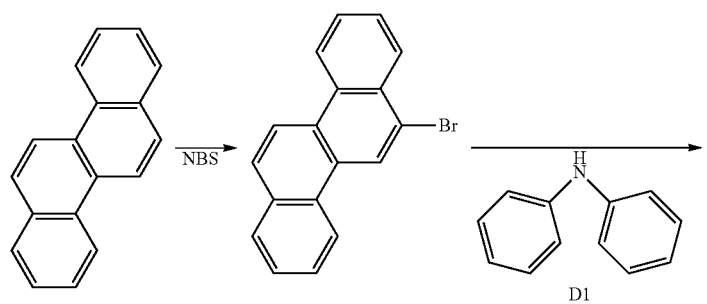
Synthetic Route 3
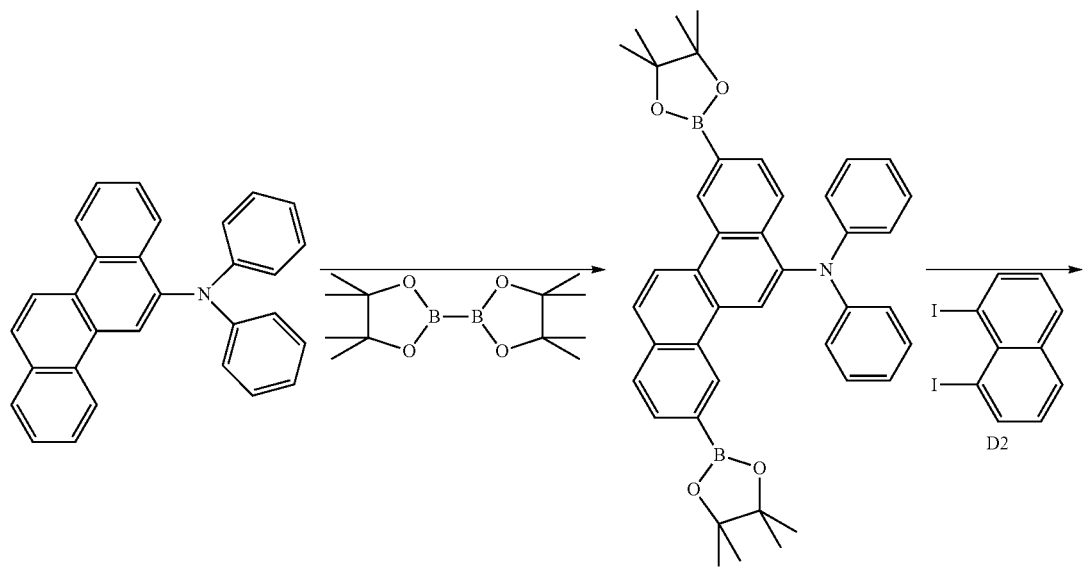

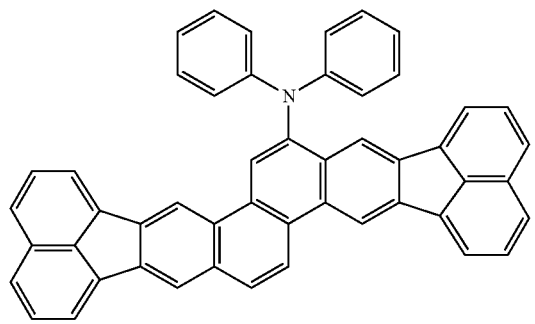
Synthetic Route 4
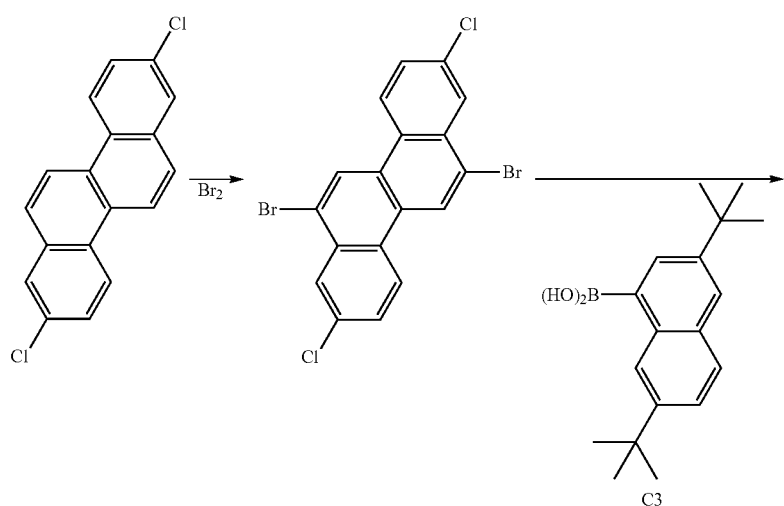
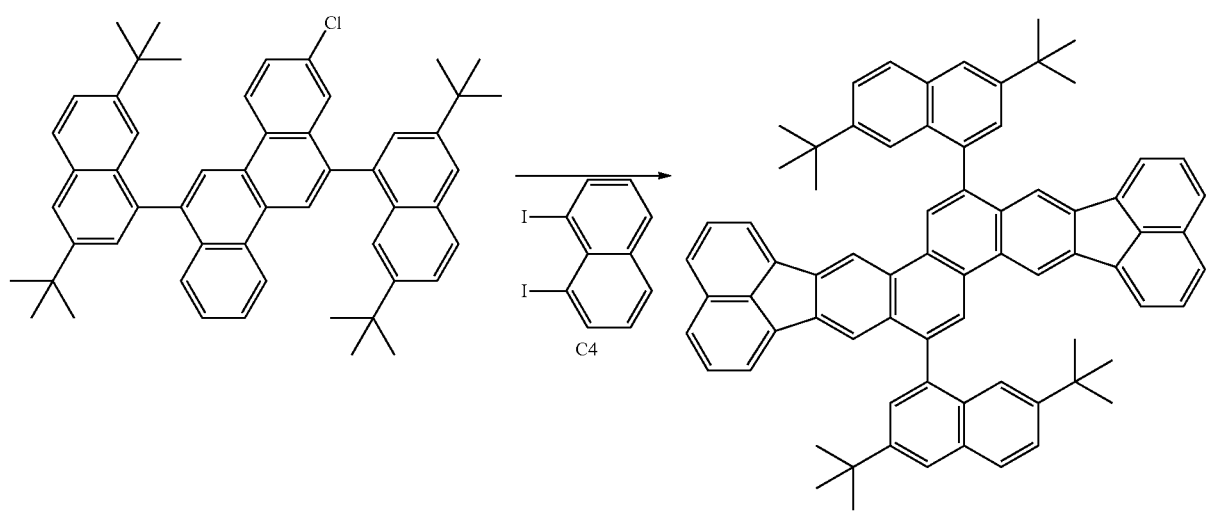
Synthetic compounds obtained in Synthetic Examples 1 to 8 are shown in the Table 1 below. Each synthetic compound is obtained through the synthetic route 1 described above but with compounds B1 and B2 in the corresponding row replacing B1 and B2 used in the synthetic route 1.

TABLE 1
| | B1 | B2 |
|---|---|---|
| Synthetic Example 1 | 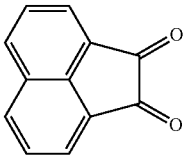 | 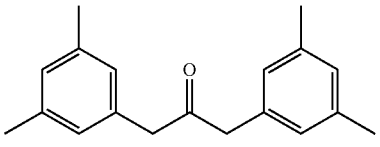 |
| Synthetic Example 2 | 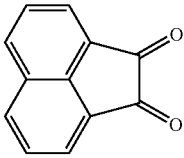 | 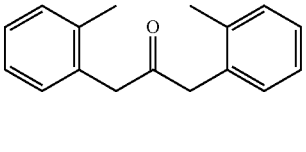 |
| Synthetic Example 3 | 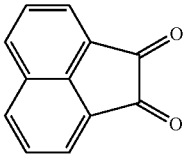 | 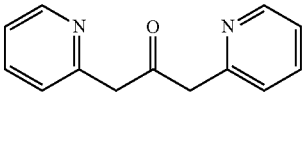 |
| Synthetic Example 4 | 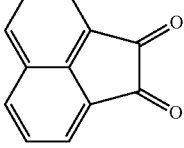 | 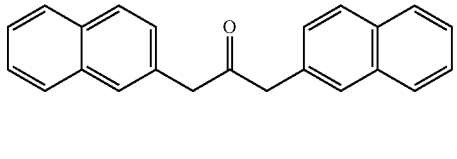 |
| Synthetic Example 5 | 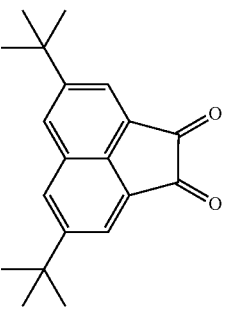 | 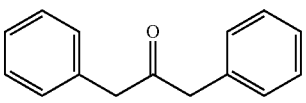 |
| Synthetic Example 6 | 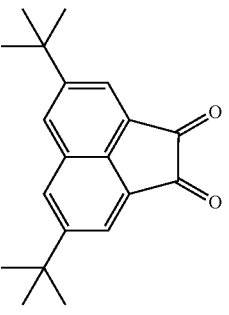 | 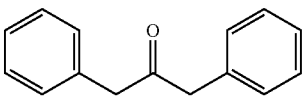 |
| Synthetic Example 7 | 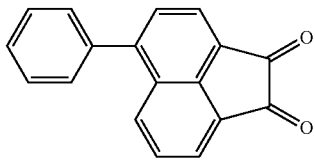 | 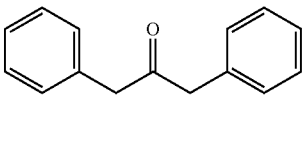 |

TABLE 1-continued
| Synthetic Example 8 | 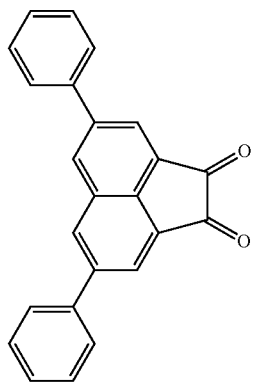 | 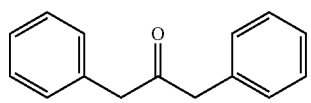 |
Synthetic compounds
Synthetic Example 1
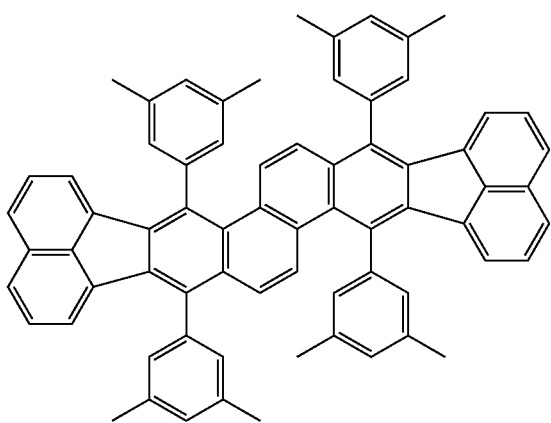 [SMILES: Cc1cc(C)cc(-c2c3c(c(-c4cc(C)cc(C)c4)c4c2ccc2c4ccc4c(-c5cc(C)cc(C)c5)c5c(c(-c6cc(C)cc(C)c6)c42)-c2cccc4cccc-5c24)-c2cccc4cccc-3c24)c1]
Synthetic Example 2
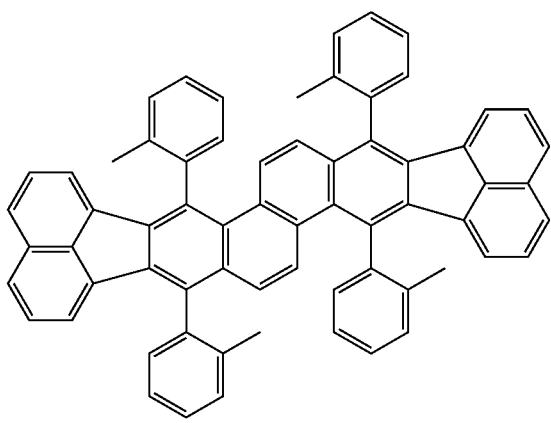 [SMILES: Cc1ccccc1-c1c2c(c(-c3ccccc3C)c3c1ccc1c3ccc3c(-c4ccccc4C)c4c(c(-c5ccccc5C)c31)-c1cccc3cccc-4c13)-c1cccc3cccc-2c13]

TABLE 1-continued
Synthetic Example 3
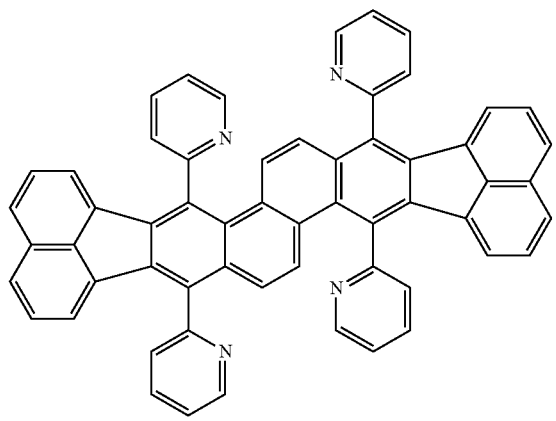 [SMILES: c1ccc(-c2c3c(c(-c4ccccn4)c4c2ccc2c4ccc4c(-c5ccccn5)c5c(c(-c6ccccn6)c42)-c2cccc4cccc-5c24)-c2cccc4cccc-3c24)nc1]
Synthetic Example 4
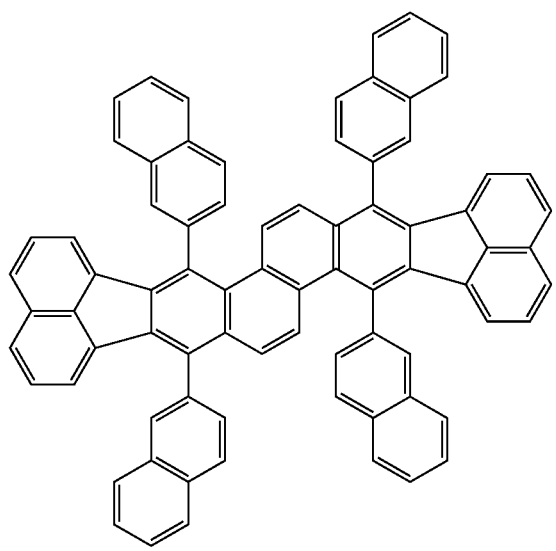 [SMILES: c1ccc2cc(-c3c4c(c(-c5ccc6ccccc6c5)c5c3ccc3c5ccc5c(-c6ccc7ccccc7c6)c6c(c(-c7ccc8ccccc8c7)c53)-c3cccc5cccc-6c35)-c3cccc5cccc-4c35)ccc2c1]
Synthetic Example 5
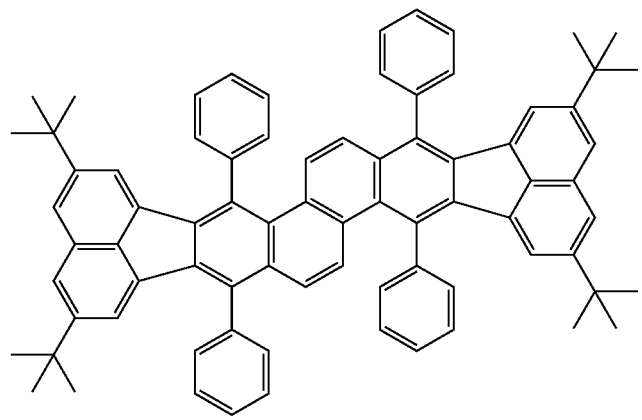 [SMILES: CC(C)(C)c1cc2c3c(cc(C(C)(C)C)cc3c1)-c1c-2c(-c2ccccc2)c2ccc3c(ccc4c(-c5ccccc5)c5c(c(-c6ccccc6)c43)-c3cc(C(C)(C)C)cc4cc(C(C)(C)C)cc-5c34)c2c1-c1ccccc1]

TABLE 1-continued
Synthetic Example 6
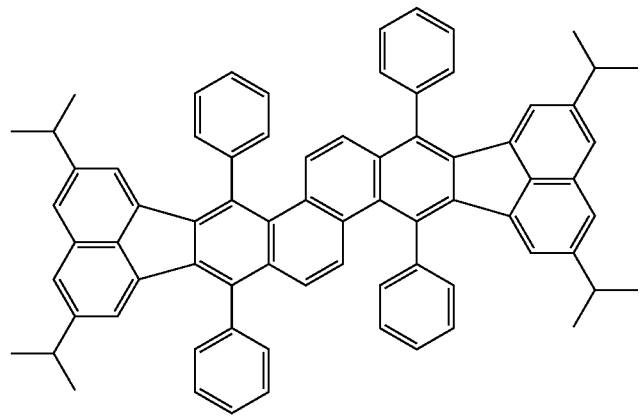 [SMILES: CC(C)c1cc2c3c(cc(C(C)C)cc3c1)-c1c-2c(-c2ccccc2)c2ccc3c(ccc4c(-c5ccccc5)c5c(c(-c6ccccc6)c43)-c3cc(C(C)C)cc4cc(C(C)C)cc-5c34)c2c1-c1ccccc1]
Synthetic Example 7
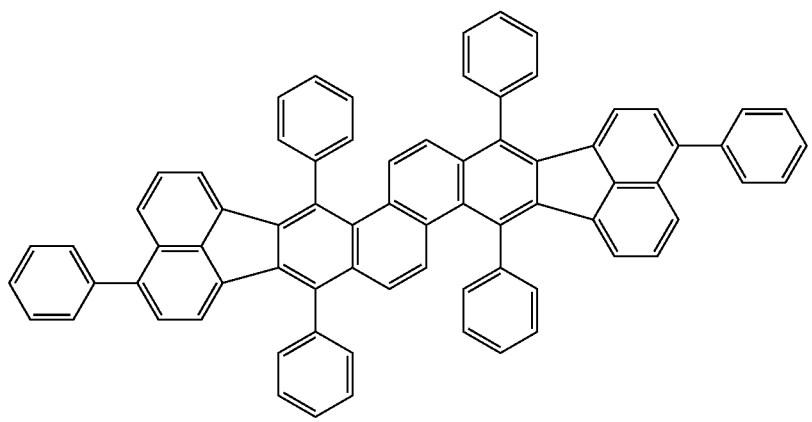 [SMILES: c1ccc(-c2ccc3c4c(cccc24)-c2c-3c(-c3ccccc3)c3ccc4c(ccc5c(-c6ccccc6)c6c(c(-c7ccccc7)c54)-c4cccc5c(-c7ccccc7)ccc-6c45)c3c2-c2ccccc2)cc1]
Synthetic Example 8
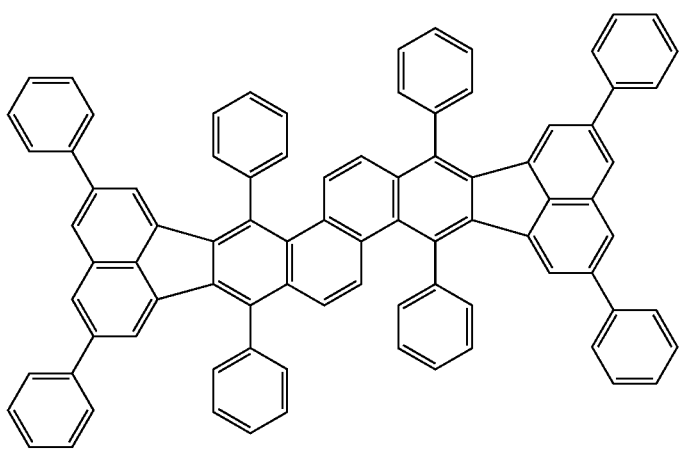 [SMILES: c1ccc(-c2cc3c4c(cc(-c5ccccc5)cc4c2)-c2c-3c(-c3ccccc3)c3ccc4c(ccc5c(-c6ccccc6)c6c(c(-c7ccccc7)c54)-c4cc(-c5ccccc5)cc5cc(-c7ccccc7)cc-6c45)c3c2-c2ccccc2)cc1]

Synthetic Examples 9 to 16 are summarized in Table 2 below. Synthetic Examples 9 to 16 show that synthetic compounds can be obtained through the synthetic route 2 or 4 by replacing compounds C1, C2, C3, and C4 described in the synthetic route 2 or 4 by those indicated in the corresponding row in Table 2 below.

Note that the synthetic routes 2 and 4 are used to synthesize the same synthetic compounds but through different synthetic pathways.

TABLE 2

| | C1 and C3 | C2 and C4 | Synthetic compounds |
| --- | --- | --- | --- |
| Synthetic Example 9 | | | |
| Synthetic Example 10 | | | |
| Synthetic Example 11 | | | |

TABLE 2-continued
| | C1 and C3 | C2 and C4 | Synthetic compounds |
|---|---|---|---|
| Synthetic Example 12 | 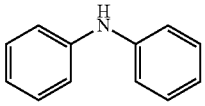 [SMILES: c1ccc(Nc2ccccc2)cc1] | 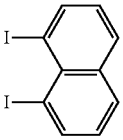 | 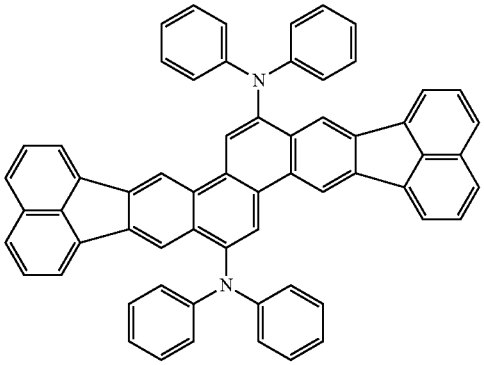 [SMILES: c1ccc(N(c2ccccc2)c2cc3c4cc5c(cc4c(N(c4ccccc4)c4ccccc4)cc3c3cc4c(cc23)-c2cccc3cccc-4c23)-c2cccc3cccc-5c23)cc1] |
| Synthetic Example 13 | 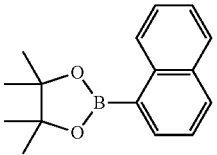 [SMILES: CC1(C)OB(c2cccc3ccccc23)OC1(C)C] | 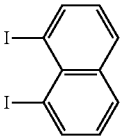 | 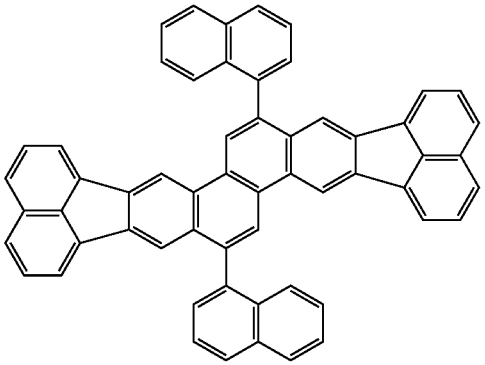 [SMILES: c1ccc2c(-c3cc4c5cc6c(cc5c(-c5cccc7ccccc57)cc4c4cc5c(cc34)-c3cccc4cccc-5c34)-c3cccc4cccc-6c34)cccc2c1] |
| Synthetic Example 14 | 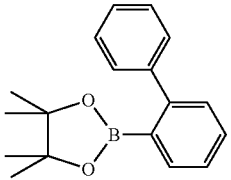 [SMILES: CC1(C)OB(c2ccccc2-c2ccccc2)OC1(C)C] | 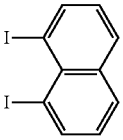 | 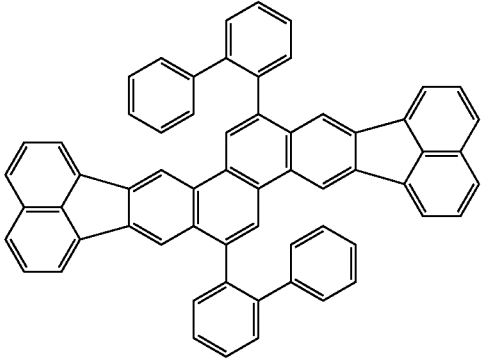 [SMILES: c1ccc(-c2ccccc2-c2cc3c4cc5c(cc4c(-c4ccccc4-c4ccccc4)cc3c3cc4c(cc23)-c2cccc3cccc-4c23)-c2cccc3cccc-5c23)cc1] |
| Synthetic Example 15 | 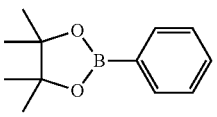 | 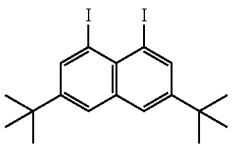 [SMILES: CC(C)(C)c1cc(I)c2c(I)cc(C(C)(C)C)cc2c1] | 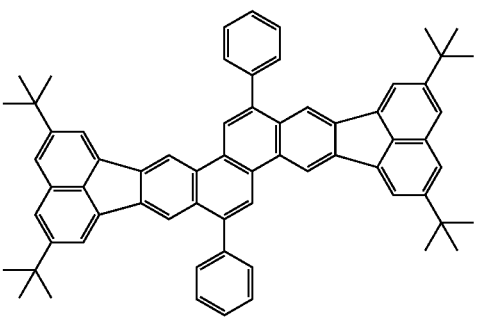 [SMILES: CC(C)(C)c1cc2c3c(cc(C(C)(C)C)cc3c1)-c1cc3c(cc1-2)c(-c1ccccc1)cc1c2cc4c(cc2c(-c2ccccc2)cc31)-c1cc(C(C)(C)C)cc2cc(C(C)(C)C)cc-4c12] |

TABLE 2-continued

| | C1 and C3 | C2 and C4 | Synthetic compounds |
|---|---|---|---|
| Synthetic Example 16 | [structure] | [structure] | [structure] |

Synthetic Examples 17 to 22 are summarized in Table 3 below. Synthetic Examples 17 to 22 show that synthetic compounds can be obtained through the synthetic route 3 by replacing compounds D1 and D2 described in the synthetic route 3 with those indicated in the corresponding row in Table 3 below.

TABLE 3

| | D1 | D2 | Synthetic compounds |
|---|---|---|---|
| Synthetic Example 17 | [structure] | [structure] | [structure] |
| Synthetic Example 18 | [structure] | [structure] | [structure] |

TABLE 3-continued

| | D1 | D2 | Synthetic compounds |
|---|---|---|---|
| Synthetic Example 19 | | | |
| Synthetic Example 20 | | | |
| Synthetic Example 21 | | | |
| Synthetic Example 22 | | | |

Next, an organic light-emitting element containing a diacenaphtho[1,2-b:1',2'-k]chrysene derivative of the present invention, i.e., a usage of the diacenaphtho[1,2-b:1',2'-k]chrysene derivative, is described.

An organic light-emitting device according to one embodiment includes a pair of electrodes, i.e., an anode and a cathode, and an organic compound layer interposed between the electrodes. This organic compound layer contains a diacenaphtho[1,2-b:1',2'-k]chrysene derivative having a backbone represented by the above-described formula or a diacenaphtho[1,2-b:1',2'-k]chrysene derivative represented by general formula (1).

In the organic light-emitting device, the organic compound interposed between the electrodes functions as a light-emitting material and emits light.

In the case where a plurality of organic compound layers are provided and one of which is an emission layer, the emission layer may be entirely or partly composed of the organic compound of the present invention.

When the emission layer is partly composed of the organic compound of the present invention, the organic compound of the present invention may be the main component or a minor component of the emission layer.

The "main component" is, for example, a component with a large content in terms of weight or moles among all compounds constituting the emission layer. The "minor component" is the component with a small content.

The material that serves as the main component can also be called a "host material".

The material that serves as a minor component can be called "dopant (guest) material", "emitting assist material", or "charge injection material".

When the organic compound of the present invention is used as a guest material, the guest material concentration relative to the host material can be 0.01 to 20 wt %, in particular, 0.5 to 10 wt %. The wavelength of the light emitted from the emission layer can be made longer than the wavelength of the solution by 5 nm to 20 nm by adjusting the concentration of the guest material in any one of these two ranges.

When the emission layer contains a host material and a guest material having a carrier transport property, the process that leads to emission includes following steps:
1. Transportation of electrons and holes inside the emission layer.
2. Generation of excitons of the host material.
3. Transfer of excitation energy among molecules of the host material.
4. Transfer of excitation energy from the host material to the guest material.

The energy transfer in the respective steps and the emission occur in competition with various deactivation processes.

Naturally, in order to enhance the emission efficiency of the organic light-emitting device, the emission quantum yield of the emission center material (e.g., guest material) itself must be high. However, one major challenge is how to efficiently transfer energy between the molecules of the host material and between the host material and the guest material. Although the exact cause of emission deterioration by electrical current is not yet clear, the inventors believe that the emission center material or the environmental changes brought to the emission center material by the nearby molecules may be attributable to the deterioration.

The inventors of the present invention have conducted various investigations and found that when a compound represented by general formula (1) of the present invention described above is used as the host or guest material or, in particular, as the guest material in the emission layer, the device outputs light highly efficiently at a high luminance and has considerably high durability.

The organic light-emitting device of this embodiment will now be described in detail.

The organic light-emitting device according to this embodiment includes a pair of electrodes, i.e., an anode and a cathode, and an organic compound layer interposed between the electrodes. The organic compound layer contains either a derivative having a diacenaphtho[1,2-b:1',2'-k]chrysene backbone or a diacenaphtho[1,2-b:1',2'-k]chrysene derivative represented by general formula (I).

One or more compound layers other than the organic compound layer may be provided between the pair of electrodes.

In other words, two or more compound layers including the organic compound layer described above may be provided between the pair of electrodes. In such a case, the organic light-emitting device is called a multilayer organic light-emitting device.

First to fifth examples of multilayer organic light-emitting devices are described below.

A first example of a multilayer organic light-emitting device is a structure in which an anode, an emission layer, and a cathode are sequentially layered on a substrate. This type of organic light-emitting device is useful when a material having all of the hole transport property, the electron transport property, and the light-emitting property by itself is used in the emission layer or when compounds having respective properties are mixed and used in the emission layer.

A second example a multilayer organic light-emitting device is a structure in which an anode, a hole transport layer, an electron transport layer, and a cathode are sequentially layered on a substrate. This type of organic light-emitting device is useful when a material having a hole transport property and a material having an electron transport property are respectively used in corresponding layers or when a material having both these properties is used in both layers in combination with a simple hole transport or electron transport substance that has no light-emitting property. In such a case, the emission layer is either the hole transport layer or the electron transport layer.

A third example of a multilayer organic light-emitting device is a structure in which an anode, a hole transport layer, an emission layer, an electron transport layer, and a cathode are sequentially layered on a substrate. In this structure, the carrier transport function and the light-emitting function are separated. Compounds respectively having a hole transport property, an electron transport property, and a light-emitting property may be adequately combined and used in the device. This significantly increases the flexibility of choices of materials. Moreover, since various different compounds with different emission wavelengths can be used, the variety of the emission hue can be widened. Carriers or excitons can be effectively confined in the center emission layer to enhance the emission efficiency.

A fourth example of a multilayer organic light-emitting device is a structure in which an anode, a hole injection layer, a hole transport layer, an emission layer, an electron transport layer, and a cathode are sequentially layered on a substrate. This structure improves the adhesiveness between the anode and the hole transport layer and improves the hole injectability, which is effective for decreasing the voltage.

A fifth example of a multilayer organic light-emitting device is a structure in which an anode, a hole transport layer, an emission layer, a hole/exciton-blocking layer, an electron transport layer, and a cathode are sequentially layered on a substrate. In this structure, a layer (hole/exciton-blocking layer) that prevents holes or excitons from reaching the cathode is interposed between the emission layer and the electron transport layer. Since a compound having a significantly high ionization potential is used in the hole/exciton-blocking layer, the emission efficiency can be effectively enhanced.

In the present invention, an emission region containing a compound represented by general formula (1) refers to a region of the emission layer described above.

The multilayer structures of the first to fifth examples are only the basic device structures and do not limit the structure of the organic light-emitting element that uses the compound of the present invention. For example, various other layer structures can be employed such as providing an insulating layer at the interface between an electrode and an organic layer, providing an adhesive layer or an interference layer, designing the electron or hole transport layer to be made up of two layers with different ionization potentials.

The compound represented by general formula (1) used in the present invention may be used in any one of the first to fifth examples described above.

In the organic light-emitting device of this embodiment, at least one organic compound represented by general formula (1) of the present invention can be contained in the organic compound-containing layer. In particular, at least one organic compound represented by general formula (1) may be used as the guest material in the emission layer.

The organic compound of the present invention may be used as the host material in the emission layer.

The organic compound of the present invention may be used in any layers other than emission layer such as a hole injection layer, a hole transport layer, a hole/exciton-blocking layer, an electron transport layer, and electron injection layer.

In addition to the organic compound of the present invention, existing low-molecular-weight and polymer hole transport compounds, light-emitting compounds, and electron transport compounds and the like may be used in combination if needed.

Examples of such compounds are as follows.

Hole injection/transport materials may have a high hole mobility so that holes can be easily injected from the anode and the injected holes can be transferred to the emission layer. Examples of the low-molecular-weight and polymer materials having hole injection/transport functions include, but are not limited to, triarylamine derivatives, phenylenediamine derivatives, stilbene derivatives, phthalocyanine derivatives, porphyrin derivatives, poly(vinyl carbazole), polythiophene, and other conductive polymers.

Examples of the host material include, but are not limited to, the compounds indicated in Table 4 and derivatives thereof; fused-ring compounds such as fluorene derivatives, naphthalene derivatives, anthracene derivatives, pyrene derivatives, carbazole derivatives, quinoxaline derivatives, and quinoline derivatives; organoaluminum derivatives such as tris(8-quinolinolato)aluminum; organic zinc complexes; and polymer derivatives such as triphenylamine derivatives, polyfluorene derivatives, and polyphenylene derivatives.

TABLE 4

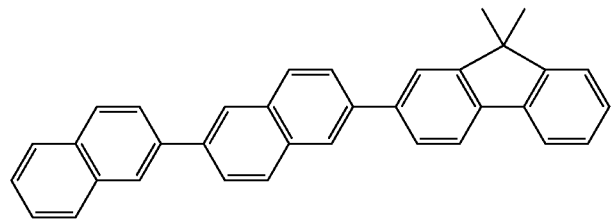 [SMILES: CC1(C)c2ccccc2-c2ccc(-c3ccc4cc(-c5ccc6ccccc6c5)ccc4c3)cc21]

H1

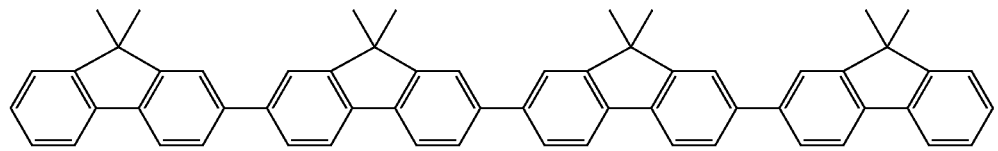 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]

H2

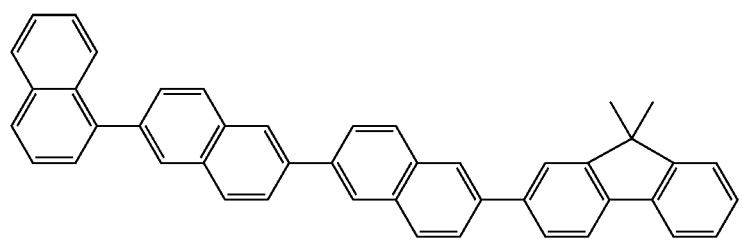 [SMILES: CC1(C)c2ccccc2-c2ccc(-c3ccc4cc(-c5ccc6cc(-c7cccc8ccccc78)ccc6c5)ccc4c3)cc21]

H3

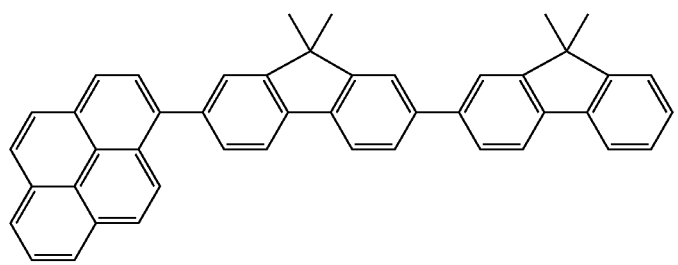 [SMILES: CC1(C)c2ccccc2-c2ccc(-c3ccc4c(c3)C(C)(C)c3cc(-c5ccc6ccc7cccc8ccc5c6c78)ccc3-4)cc21]

H4

TABLE 4-continued
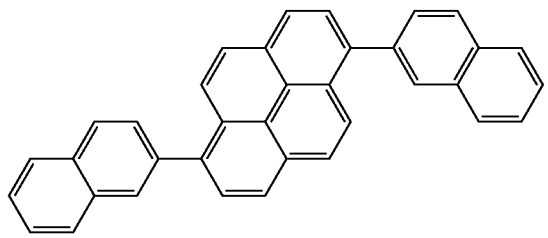 [SMILES: c1ccc2cc(-c3ccc4ccc5c(-c6ccc7ccccc7c6)ccc6ccc3c4c65)ccc2c1]
H5
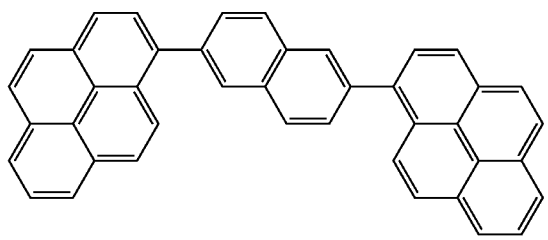 [SMILES: c1cc2ccc3ccc(-c4ccc5cc(-c6ccc7ccc8cccc9ccc6c7c89)ccc5c4)c4ccc(c1)c2c34]
H6
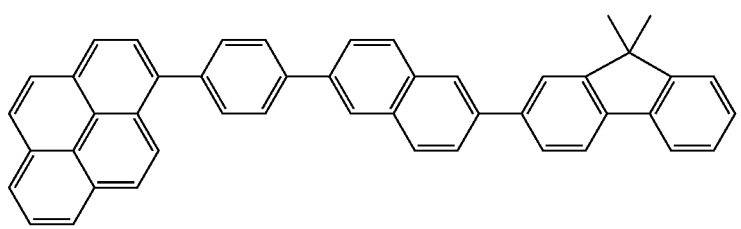 [SMILES: CC1(C)c2ccccc2-c2ccc(-c3ccc4cc(-c5ccc(-c6ccc7ccc8cccc9ccc6c7c89)cc5)ccc4c3)cc21]
H7
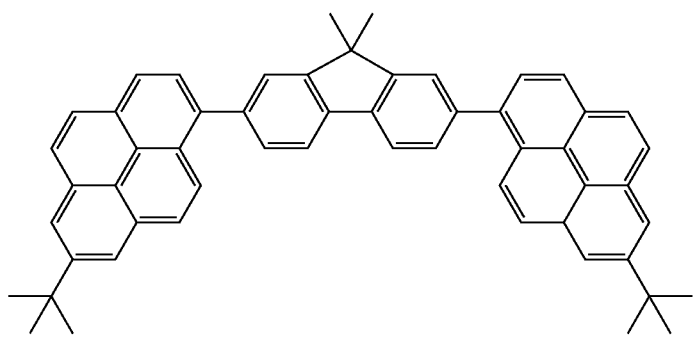
H8
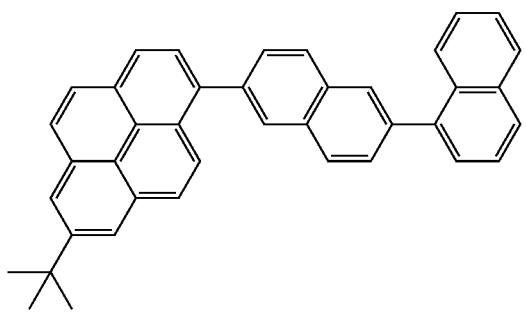 [SMILES: CC(C)(C)c1cc2ccc3ccc(-c4ccc5cc(-c6cccc7ccccc67)ccc5c4)c4ccc(c1)c2c34]
H9

TABLE 4-continued
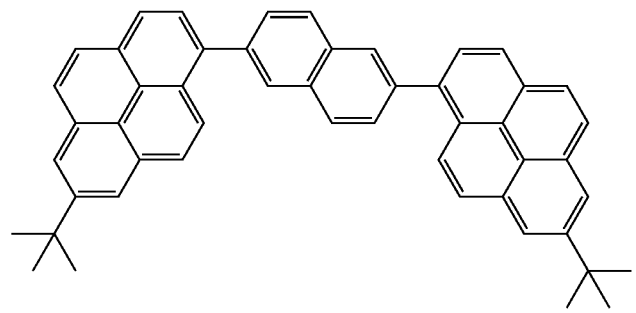 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
H10
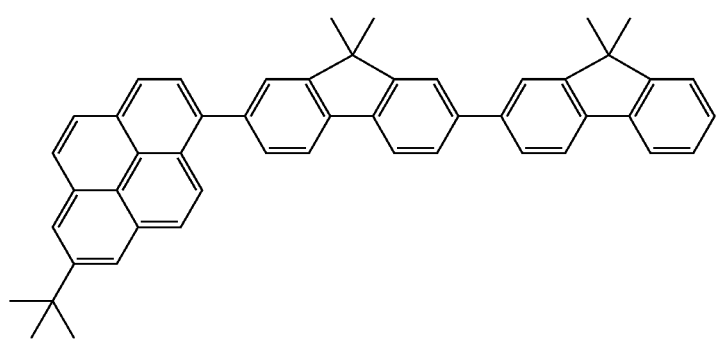 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]
H11
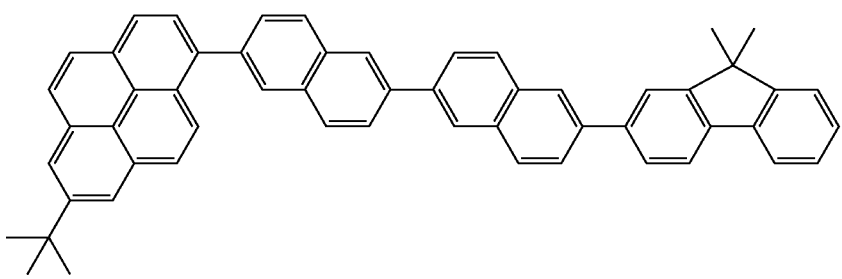 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34]
H12
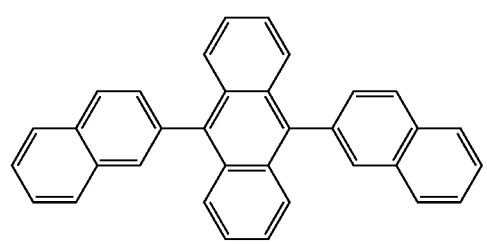 [SMILES: c1ccc2cc(-c3c4ccccc4c(-c4ccc5ccccc5c4)c4ccccc34)ccc2c1]
H13
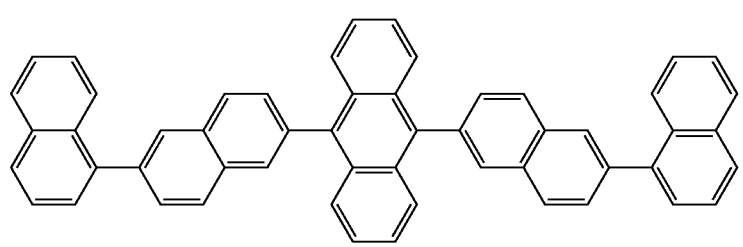 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H14

TABLE 4-continued
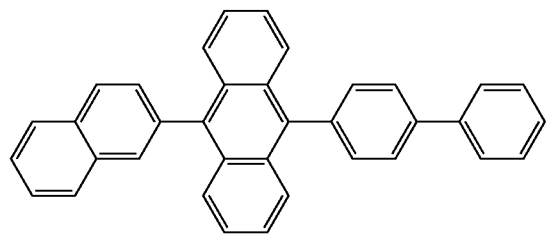 [SMILES: c1ccc(-c2ccc(-c3c4ccccc4c(-c4ccc5ccccc5c4)c4ccccc34)cc2)cc1]
H15
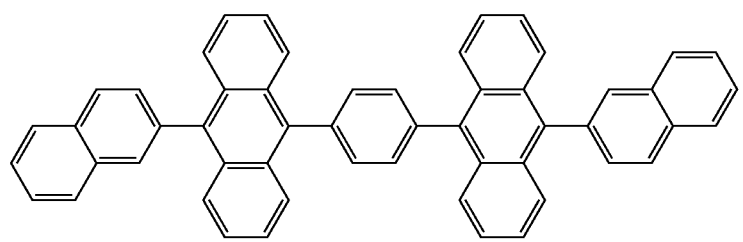 [SMILES: c1ccc2cc(-c3c4ccccc4c(-c4ccc(-c5c6ccccc6c(-c6ccc7ccccc7c6)c6ccccc56)cc4)c4ccccc34)ccc2c1]
H16
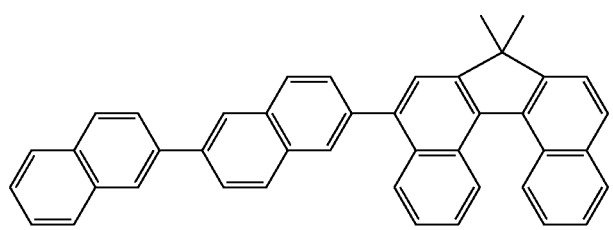 [SMILES: CC1(C)c2ccc3ccccc3c2-c2c1cc(-c1ccc3cc(-c4ccc5ccccc5c4)ccc3c1)c1ccccc21]
H17
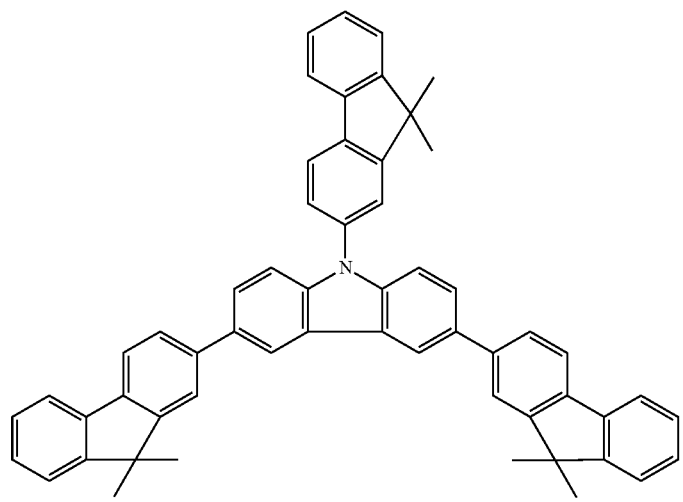 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H18

TABLE 4-continued
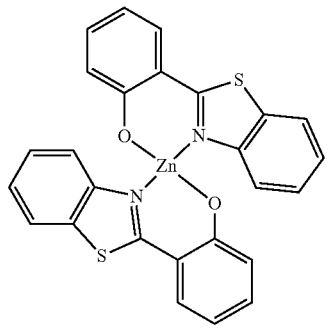
H19
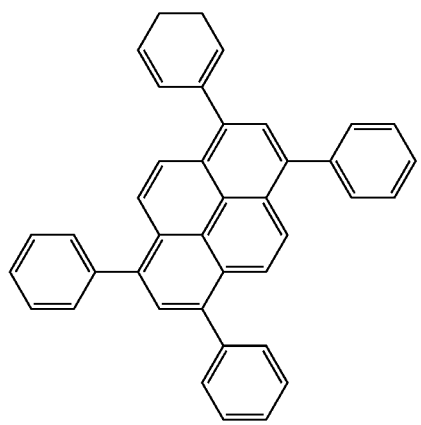 [SMILES: C1=CC(c2cc(-c3ccccc3)c3ccc4c(-c5ccccc5)cc(-c5ccccc5)c5ccc2c3c54)=CCC1]
H20
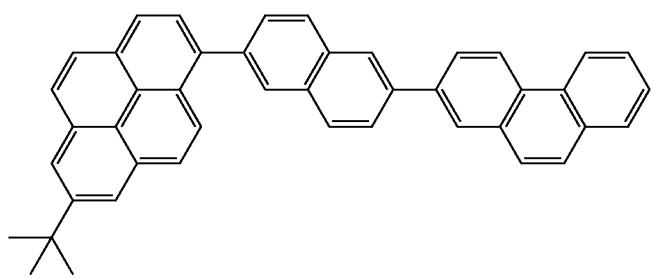 [SMILES: CC(C)(C)c1cc2ccc3ccc(-c4ccc5cc(-c6ccc7c(ccc8ccccc87)c6)ccc5c4)c4ccc(c1)c2c34]
H21
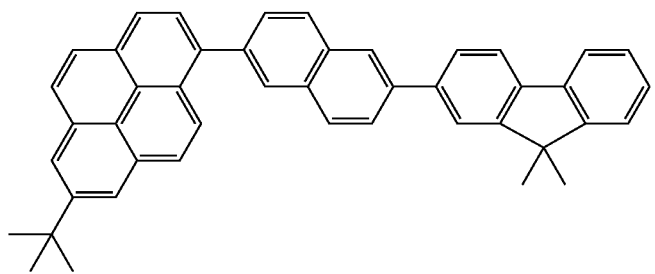 [SMILES: CC(C)(C)c1cc2ccc3ccc(-c4ccc5cc(-c6ccc7c(c6)C(C)(C)c6ccccc6-7)ccc5c4)c4ccc(c1)c2c34]
H22

TABLE 4-continued
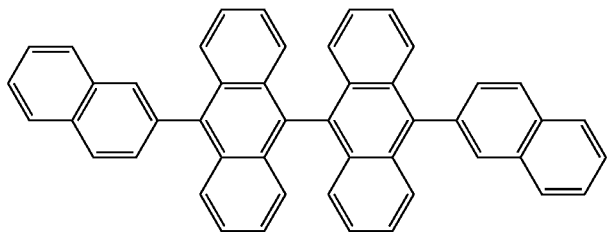 [SMILES: c1ccc2cc(-c3c4ccccc4c(-c4c5ccccc5c(-c5ccc6ccccc6c5)c5ccccc45)c4ccccc34)ccc2c1]
H23
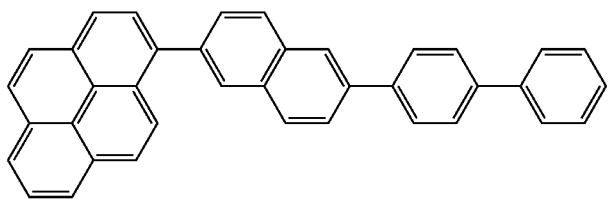 [SMILES: c1ccc(-c2ccc(-c3ccc4cc(-c5ccc6ccc7cccc8ccc5c6c78)ccc4c3)cc2)cc1]
H24
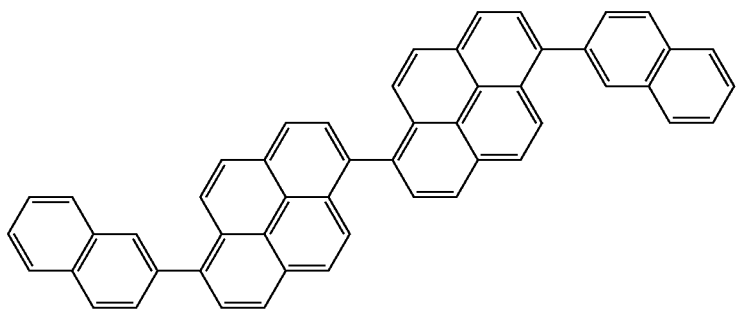 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1]
H25
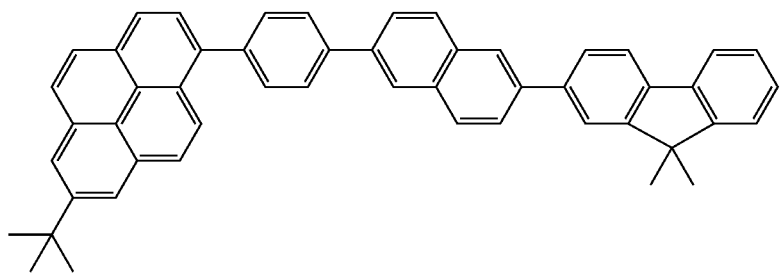 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34]
H26
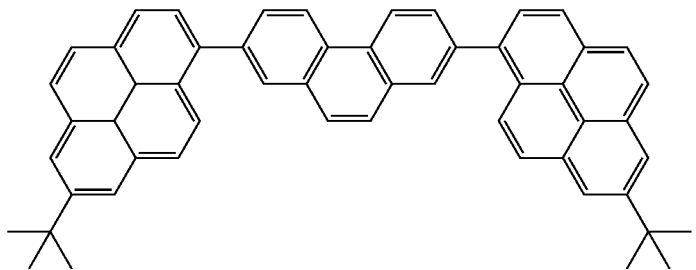 [SMILES: CC(C)(C)C1=CC2=CC=C3C(c4ccc5c(ccc6cc(-c7ccc8ccc9cc(C(C)(C)C)cc%10ccc7c8c9%10)ccc65)c4)=CC=C4C=CC(=C1)C2C43]
H27

TABLE 4-continued

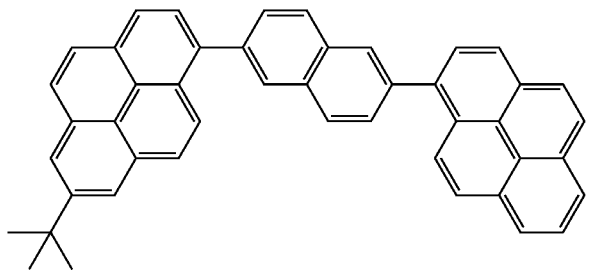 [SMILES: CC(C)(C)c1cc2ccc3ccc(-c4ccc5cc(-c6ccc7ccc8cccc9ccc6c7c89)ccc5c4)c4ccc(c1)c2c34]

H28

The hole injection/transport material can be adequately selected from those that allow easy injection of electrons from the cathode and transport the injected electrons to the emission layer. A material is selected by considering the balance with the hole mobility of the hole injection/transport material and the like. Examples of the materials having electron injection/transport properties include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

The material for the anode may be a material that has a high work function. Examples thereof include single metals such as gold, platinum, silver, copper, nickel, palladium, cobalt, selenium, vanadium, and tungsten, and their alloys; and metal oxides such as tin oxide, zinc oxide, indium oxide, indium tin oxide (ITO), and zinc indium oxide. Electrically conductive polymers such as polyaniline, polypyrrole, polythiophene, and the like can also be used. These electrode substances may be used alone or in combination. The anode may have a single-layer structure or a multilayer structure.

In contrast, the material for the cathode may be a material that has a low work function. Examples of such a material include alkali metals such as lithium, alkaline earth metals such as calcium, and other single metals such as aluminum, titanium, manganese, silver, lead, and chromium. Alternatively, an alloy combining these single metals may also be used. Examples thereof include magnesium-silver, aluminum-lithium, and aluminum-magnesium. Metal oxides such as indium tin oxide (ITO) may also be used. These electrode substances may be used alone or in combination. The cathode may have a single-layer structure or a multilayer structure.

The substrate used in the organic light-emitting device of this embodiment is not particularly limited. For example, an opaque substrate such as a metal substrate or a ceramic substrate, or a transparent substrate such as a glass substrate, a quartz substrate, or a plastic sheet, may be used. A color filter film, a fluorescence color conversion filter film, a dielectric reflective film, or the like may be formed on the substrate to control the color of emission.

A protective layer or a sealing layer may be provided to the fabricated device in order to prevent the device from contacting oxygen, moisture, and the like.

Examples of the protective layer include inorganic material films such as diamond thin films and metal oxide and metal nitride films; polymeric films of fluorocarbon resin, polyethylene, silicone resin, and polystyrene resin; and films of photocurable resin. The device may be covered with glass, a gas-impermeable film, a metal, or the like and packaged with an adequate sealing resin.

In the organic light-emitting device of this embodiment, a layer containing the organic compound of the present invention and layers containing other organic compounds are formed by the following methods. In general, thin films are formed by vacuum vapor deposition, ionization deposition, sputtering, plasma-enhanced deposition, and various existing coating techniques (e.g., spin-coating, dipping, casting, a Langmuir-Blodgett technique, and ink-jet) that involves dissolving the compounds in adequate solvents. When layers are formed by vacuum vapor deposition or a solution coating technique, crystallization and other unfavorable phenomena rarely occur and stability with time is excellent. When a coating technique is used to form films, an adequate binder resin may be used in combination.

Examples of the binder resin include, but are not limited to, polyvinyl carbazole resin, polycarbonate resin, polyester resin, ABS resin, acryl resin, polyimide resin, phenol resin, epoxy resin, silicone resin, and urea resin. These binder resins may be used alone as a homopolymer or in combination as a copolymer. If needed, existing additives such as a plasticizer, an antioxidant, and a UV absorber may be used in combination.

The organic light-emitting device of this embodiment can be applied to products that require energy saving and high luminance. Examples of the application include light sources of display apparatuses, lighting apparatuses, and printers, and backlights for liquid crystal display apparatuses.

When the organic light-emitting device is applied to a display apparatus, a high-visibility, light-weight, energy-saving flat panel display can be made. The display apparatus can be used as image-display apparatuses for personal computers, televisions, and advertising media. The display apparatus may be used in a display unit of an image-capturing apparatuses such as digital still cameras and digital video cameras.

Alternatively, the display apparatus may be used in an operation display unit of an electrophotographic image-forming apparatus, e.g., a laser beam printer or a copier.

The organic light-emitting device may be used as a light source for exposing a latent image on a photosensitive member of an electrophotographic image-forming apparatus, e.g., a laser beam printer or a copier. A plurality of organic light-emitting devices that can be addressed independently may be arranged into an array (e.g., lines) and desired exposure may be conducted on a photosensitive drum to form a latent image. Since the organic light-emitting devices of this embodiment are used, the space which has been previously required for placing polygon mirrors, various optical lenses, and the like can be saved.

When the device is applied to lighting apparatuses and backlights, the effect of energy conservation can be expected. The organic light-emitting device of this embodiment can also be used as a flat light source.

Alternatively, a color filter film, a fluorescence color conversion filter film, a dielectric reflective film, and other associated components may be formed on the substrate supporting the organic light-emitting device of this embodiment to control the color of emission. A thin film transistor (TFT) may be formed on the substrate and be connected to the organic light-emitting device to control ON and OFF of the emission. A plurality of organic light-emitting devices may be arranged into a matrix, i.e., arranged in an in-plane direction, so that they can be used as a lighting apparatus.

Next, a display apparatus that uses the organic light-emitting device of this embodiment is described in detail. The display apparatus includes the organic light-emitting device of this embodiment and a unit configured to supply electrical signals to the organic light-emitting device of this embodiment. The display apparatus of this embodiment is described in detail below by taking an active matrix system as an example with reference to the drawings.

FIG. 1 is a schematic diagram illustrating an example of configuration of a display apparatus according to one embodiment. The display apparatus includes the organic light-emitting device of the embodiment and a unit configured to supply electrical signals to the organic light-emitting device of the embodiment.

Figure 2:
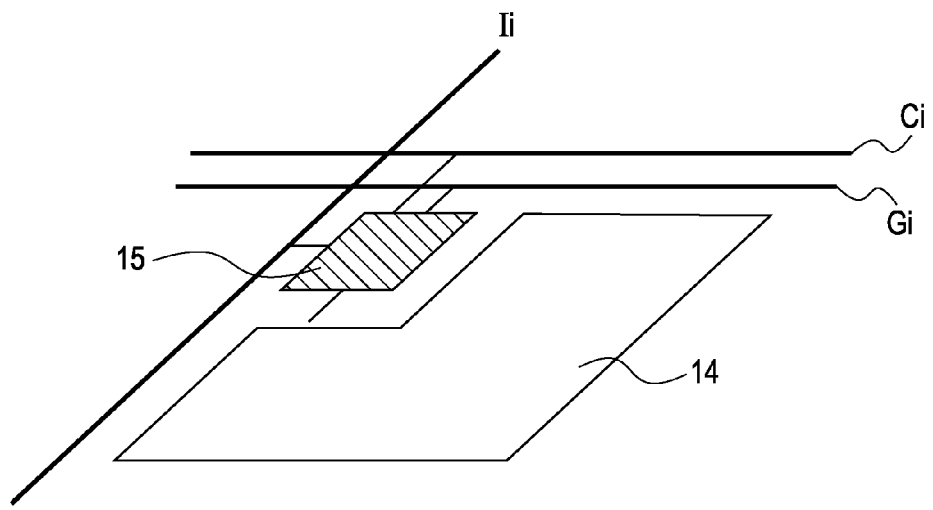
FIG. 2 is a diagram showing a pixel circuit connected to a pixel and lines connected to the pixel circuit.

FIG. 2 is a schematic diagram showing a pixel circuit connected to a pixel and signal and electrical current supply lines connected to the pixel circuit.

The unit configured to supply electrical signals to organic light-emitting device of the embodiment includes a scan signal driver 11, a data signal driver 12, and an electrical current supply source 13 in FIG. 1 and a pixel circuit 15 in FIG. 2.

A display apparatus 1 shown in FIG. 1 includes the scan signal driver 11, the data signal driver 12, and the electrical current supply source 13 which are respectively connected to gate selection lines G, data signal lines I, and electrical current supply lines C, Pixel circuits 15 are arranged at intersections of the gate selection lines G and the data signal lines I, as shown in FIG. 2. One pixel 14 constituted by the organic light-emitting device of the embodiment is provided for each corresponding pixel circuit 15. In other words, the pixel 14 is an organic light-emitting device. In the drawing, the organic light-emitting device is illustrated as the emission point. Upper electrodes of the organic light-emitting devices may be formed as a common upper electrode for all of the organic light-emitting devices. Of course, the upper electrodes of the respective organic light-emitting devices may be formed separately.

The scan signal driver 11 sequentially selects gate selection lines G1, G2, G3, . . . and Gn, in synchronization with which image signals are applied to the pixel circuits 15 via one of data signal lines I1, I2, I3, . . . and In from the data signal driver 12.

Figure 3:
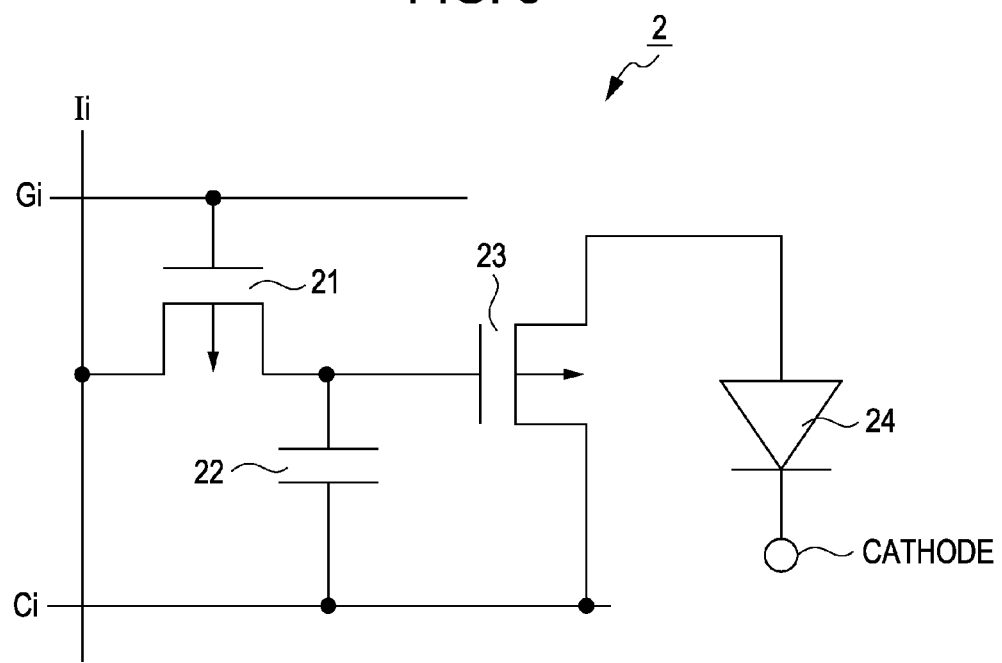
FIG. 3 is a circuit diagram showing the pixel circuit.

Next, operation of a pixel is described. FIG. 3 is a circuit diagram showing a circuit configuring one pixel in the display apparatus 1 shown in FIG. 1. In FIG. 3, a second thin film transistor (TFT) 23 controls the electrical current for causing an organic light-emitting device 24 to emit light. In a pixel circuit 2 in FIG. 3, when a selection signal is applied to a gate select on line Gi, the first TFT 21 is turned ON, an image signal Ii is supplied to a capacitor 22, and a gate voltage of the second TFT 23 is thereby determined. An electrical current is supplied to the organic light-emitting device 24 from an electrical current supply line Ci according to the gate voltage of the second TFT 23. Here, the gate potential of the second TFT 23 is retained in the capacitor 22 until the first TFT 21 is scanned and selected next. Accordingly, the electric current keeps flowing in the organic light-emitting device 24 until the next time scanning is performed. As a result, the organic light-emitting device 24 keeps emitting light during one frame period.

Although not shown in the drawings, the organic light-emitting device of this embodiment can be used in a voltage-write display apparatus in which the voltage between the electrodes of the organic light-emitting device 24 is controlled by a thin film transistor.

Figure 4:
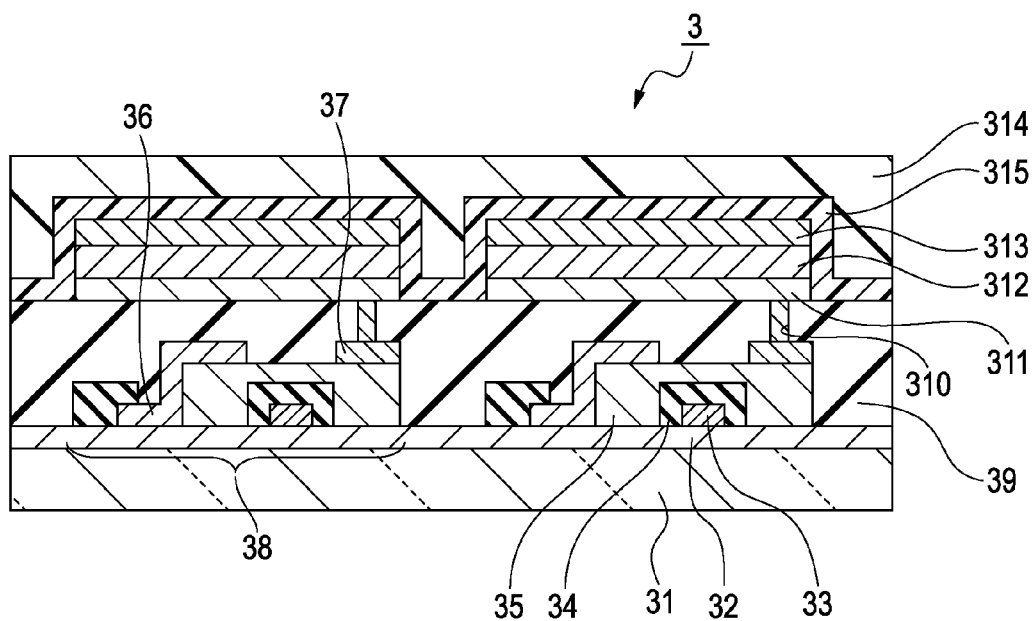
FIG. 4 is a schematic cross-sectional view of an organic light-emitting device and a thin film transistor under the organic light-emitting device.

FIG. 4 is a schematic view showing one example of a cross-sectional structure of a TFT substrate used in the display apparatus shown in FIG. 1. The detailed structure is described below by taking a method for making the TFT substrate as an example.

In making a display apparatus 3 shown in FIG. 4, first, a moisture-proof film 32 for protecting components (FT or organic layer) formed thereon is formed on a substrate 31 composed of glass or the like by coating. Silicon oxide or a complex of silicon oxide and silicon nitride is used to form the moisture-proof film 32. Next, a metal film of Cr or the like is formed by sputtering and patterned into a particular circuit shape to form a gate electrode 33.

A film of silicon oxide or the like is formed by plasma-enhanced CVD or catalytic chemical vapor deposition (cat-CVD) and patterned to form a gate insulating film 34. A silicon film is formed by plasma-enhanced CVD or the like (annealing at a temperature of 290° C. or more if necessary) and patterned according to a circuit shape to form a semiconductor layer 35.

A drain electrode 36 and a source electrode 37 are formed on the semiconductor layer 35 to form a TFT element 38. As a result, a circuit as shown in FIG. 3 is formed. The TFT element 38 is a switching element connected to the organic light-emitting device and switches the light emission ON and OFF for the organic light-emitting device. Next, an insulating film 39 is formed on the TFT element 38. A contact hole (through hole) 310 is formed to connect a metal anode 311 for the organic light-emitting device to the source electrode 37.

A multilayer or single-layer organic layer 312 and a cathode 313 are sequentially layered on the anode 311. As a result, the display apparatus 3 is obtained. A first protective layer 314 and a second protective layer 315 may be provided to prevent deterioration of the organic light-emitting device. In operation, the display apparatus using the organic light-emitting device of this embodiment can achieve stable display of high-quality images for a long period of time.

Note that the switching element of the display apparatus described above is not particularly limited, and the display apparatus can be applied even with a singe crystal silicon substrate, a MIM device, an a-Si device, or the like.

An organic light-emitting display panel can be obtained by sequentially layering a single-layer or multilayer organic emission layer and a cathode layer on the ITO electrode. In operation, the display panel using the organic compound of this embodiment can achieve stable display of high-quality images for a long period of time.

As for the direction in which the light is output from the device, either a bottom-emission structure (light is output from the substrate side) or a top-emission structure (light is output from the side opposite the substrate) is applicable.

EXAMPLES

The present invention will now be described in further detail by using non-limiting examples.

Example 1

Synthesis of Example Compound A3

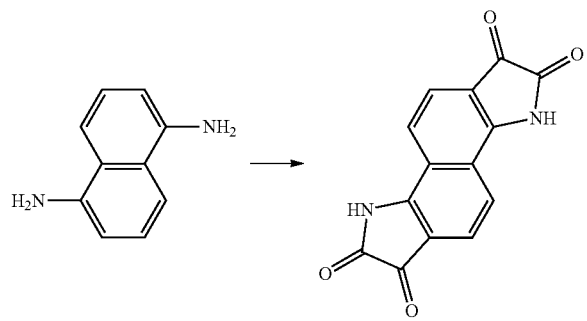 [SMILES: Nc1cccc2c(N)cccc12 ; O=c1[nH]c2c(ccc3c2ccc2c(=O)c(=O)[nH]c23)c1=O]

Into a 500 ml round-bottomed flask, 11.82 g (110 mmol) chloral hydrate, 113.6 g (800 mmol) sodium sulfate, and 400 ml water were charged, and the resulting mixture was heated to 40° C. Into a 100 ml round-bottomed flask, 7.91 g (50 mmol) 1,5-diaminonaphthalene, 60 ml water, and 8.75 ml 12N hydrochloric acid were charged, and into a 200 ml round-bottomed flask, 22.9 g (330 mmol) hydroxylamine hydrochloride and 100 ml of water were charged. After each resulting mixture was suspended or dissolved, the mixtures were sequentially added to the 500 ml rounded flask under vigorous stirring. After addition, stirring was conducted at 80° C. for 1 hour. After cooling, the precipitates were filtered, washed with water, and dried to obtain a black powder. The black powder was gradually charged into a 100 ml round-bottomed flask with 30 ml concentrated sulfuric acid heated to 60° C. while preventing the inner temperature from increasing. Stirring followed for 30 minutes. After cooling, the content was discharged on 200 g of ice. The precipitates were filtered, washed with warm water, and dried to obtain 8 g of a black powder.

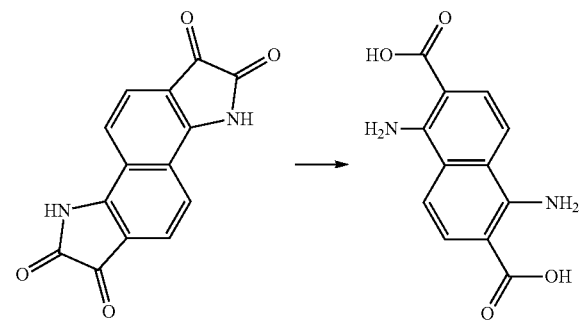 [SMILES: O=c1[nH]c2c(ccc3c2ccc2c(=O)c(=O)[nH]c23)c1=O ; Nc1c(C(=O)O)ccc2c(N)c(C(=O)O)ccc12]

Into a 300 ml round-bottomed flask, 5.3 g black power and 80 ml 10% aqueous potassium hydroxide solution were charged, and the resulting mixture was heated to 40° C. After 23 ml of a 30% hydrogen peroxide solution was slowly added dropwise, stirring was conducted at 80° C. for 1 hour. After cooling, pH was adjusted to 4 using hydrochloric acid. The precipitates were filtered and washed with water to obtain 1.5 g of a black powder.

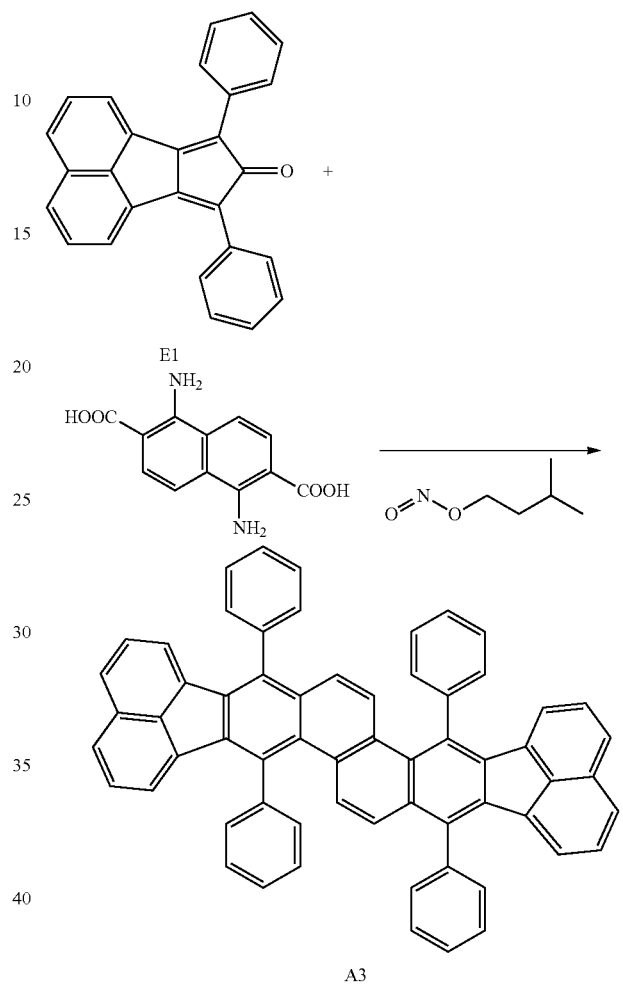

Into a 200 ml round-bottomed flask, 246 mg black powder, 712 mg (2 mmol) E1, and 50 ml toluene were charged, and the resulting mixture was heated to 80° C. After 234 mg (2 mmol) of isoamyl nitrite was slowly added dropwise, stirring was conducted at 110° C. for 3 hours. After cooling, the mixture was washed twice with 100 ml of water each time. The organic layer was washed with saturated saline and dried with magnesium sulfate. The resulting solution was filtered and concentrated to obtain a brown liquid. After the brown liquid had been purified by column chromatography (toluene/heptane=1:1), recrystallization was conducted with chloroform/methanol to obtain 20 mg (yield 1.2%) of compound A3 in form of yellow crystals.

The structure of the compound was confirmed by NM spectroscopy.

$^1$H NMR (CDCl$_3$, 500 MHz) σ (ppm): 7.98 (d, 2H, J=9.5 Hz), 7.70-7.62 (m, 20H), 7.52 (d, 4H, J=7.0 Hz), 7.51-7.20 (m, 6H), 6.50 (d, 2H, J=7.0 Hz), 6.31 (d, 2H, J=7.5 Hz).

The emission spectrum of a 1×10⁻⁵ mol/l toluene solution of Example Compound A3 was measured with F-4500 produced by Hitachi Ltd., and photoluminescence was measured at a 350 nm excitation wavelength. The spectrum had the maximum intensity at 459 nm.

Example 2

Synthesis of Example Compound A1

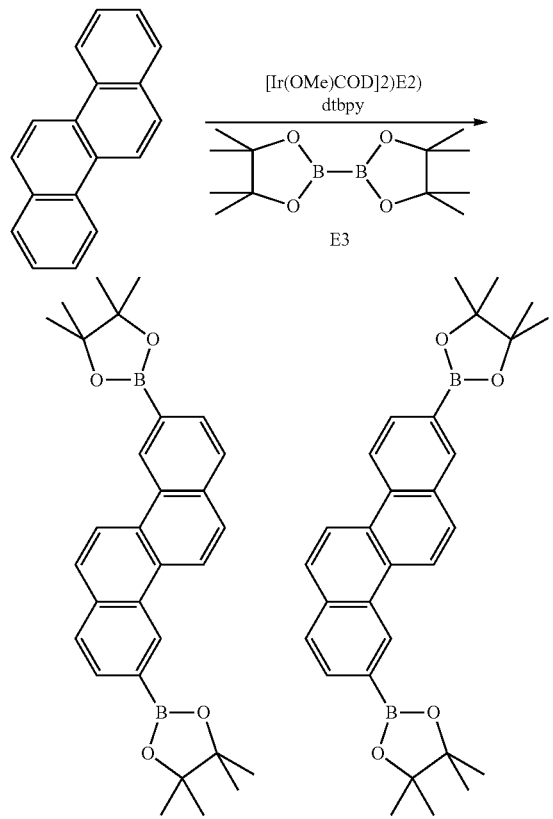

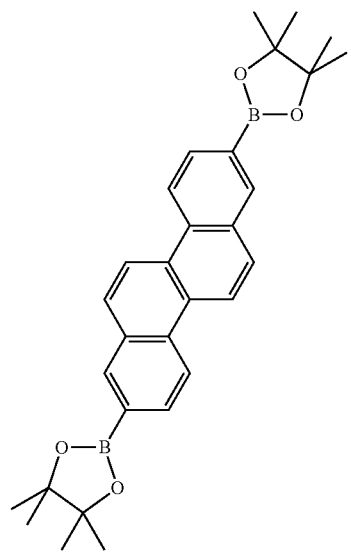

Into a 50 ml round-bottomed flask, 550 mg (2 mmol) chrysene, 50 mg (0.1 mmol) E2, 54 mg (0.2 mmol) 4,4'-di-tert-butyl-2,2'-bipyridine, 559 mg (2.2 mmol) E3, and 10 ml cyclohexane were charged. The resulting mixture was stirred for 10 hours at 80° C. After cooling, the organic layer was washed with saturated saline and dried with magnesium sulfate. The resulting solution was filtered and concentrated to obtain a brown liquid. After the brown liquid had been purified by column chromatography (toluene), recrystallization was conducted with methanol/heptane to obtain 350 mg (yield: 55%) of a mixture in form of white crystals.

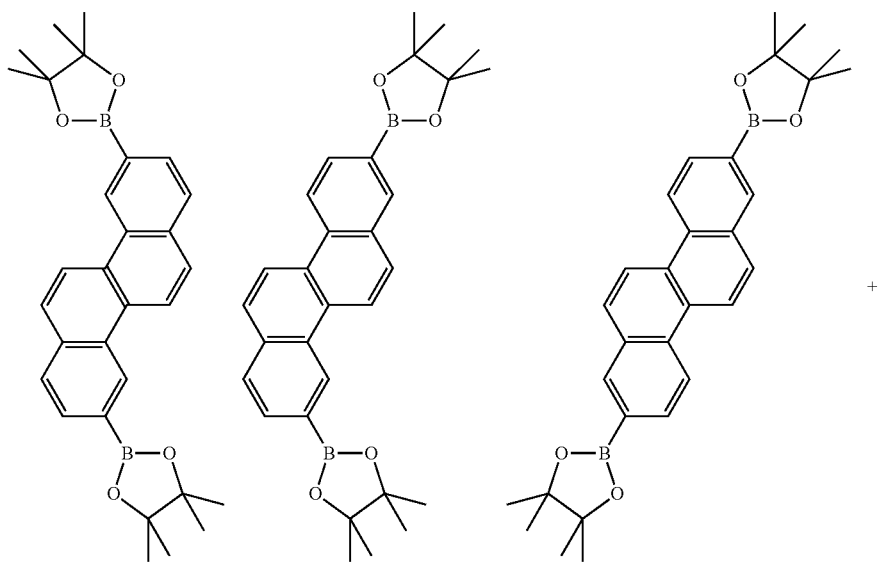

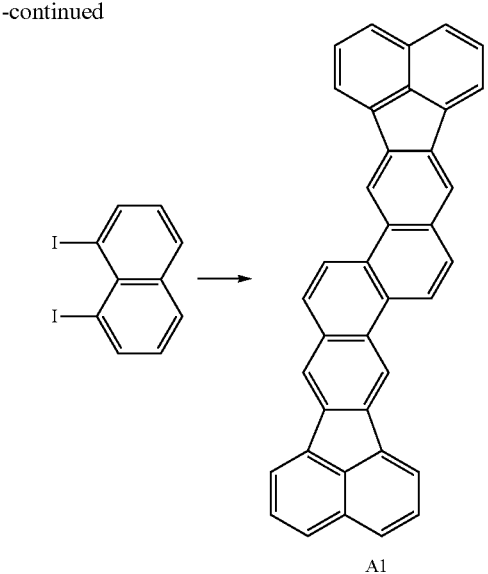

A1

Into a 10 ml round-bottomed flask, 144 mg (0.3 mmol) white crystal mixture, 228 mg (0.6 mmol) 1,8-diiodonaphthalene, 62 mg (0.06 mmol) Pd$_2$(dba)$_3$, 67 mg (0.24 mmol) tricyclohexylphosphine, 0.5 ml DBU, and 5 ml dimethylformamide were charged, and the resulting mixture was stirred at 160° C. for 5 hours. After cooling, the organic layer was washed with saturated saline and dried with magnesium sulfate. The resulting solution was filtered and concentrated to obtain a brown liquid. After the brown liquid had been purified by column chromatography (chloroform/heptane), recrystallization was conducted with methanol/heptane to obtain 50 mg (yield 10%) of compound A1 in form of yellow crystals.

The emission spectrum of a 1×10$^{-5}$ mol/l toluene solution of Example Compound A1 was measured with F-4500 produced by Hitachi Ltd., and photoluminescence was measured at a 350 nm excitation wavelength. The spectrum had the maximum intensity at 440 nm.

Example 3

Synthesis of Example Compound A11

Example Compound A11 was synthesized as in Example 2 except that chrysene used as the raw material was changed to E4:

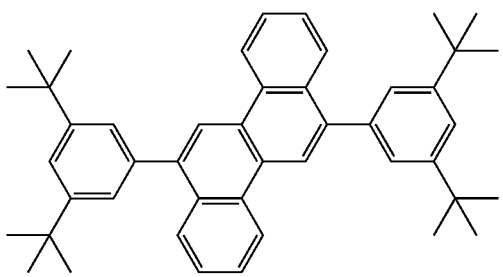

E4

The emission spectrum of a 1×10$^{-5}$ mol/l toluene solution of Example Compound A11 was measured with F-4500 produced by Hitachi Ltd., and photoluminescence was measured at a 350 nm excitation wavelength. The spectrum had the maximum intensity at 455 nm.

Example 4

Synthesis of Example Compound A76

Example Compound A76 was synthesized as in Example except that chrysene was changed to E5:

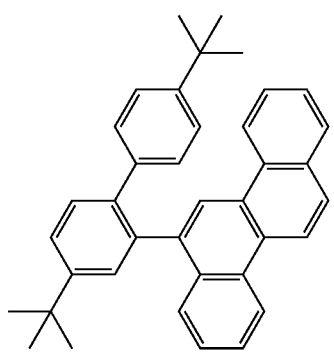

E5

The emission spectrum of a 1×10$^{-5}$ mol/l toluene solution of Example Compound A76 was measured with F-4500 produced by Hitachi Ltd., and photoluminescence was measured at a 350 nm excitation wavelength. The spectrum had the maximum intensity at 450 nm.

Examples 5 to 20

In Examples 5 to 20, multilayer organic light-emitting devices of the fifth example (anode/hole injection layer/hole transport layer/emission layer/hole- and exciton-blocking layer/electron transport layer/cathode) were prepared. In each example, an ITO film 100 nm in thickness was formed on a glass substrate by patterning. The following organic and electrode layers were then continuously formed on the ITO substrate by resistance heating vapor deposition in a vacuum chamber at $10^{-5}$ Pa so that the area of the electrodes facing each other was 3 mm$^2$.

Hole transport layer (30 nm): F-1
Emission layer (30 nm), Host: F-2, Guest: Example Compound (weight ratio: 5%)
Hole/exciton-blocking layer (10 nm): F-3
Electron transport layer (30 nm): F-4
Metal electrode layer 1 (1 nm): LiF
Metal electrode layer 2 (100 nm): Al

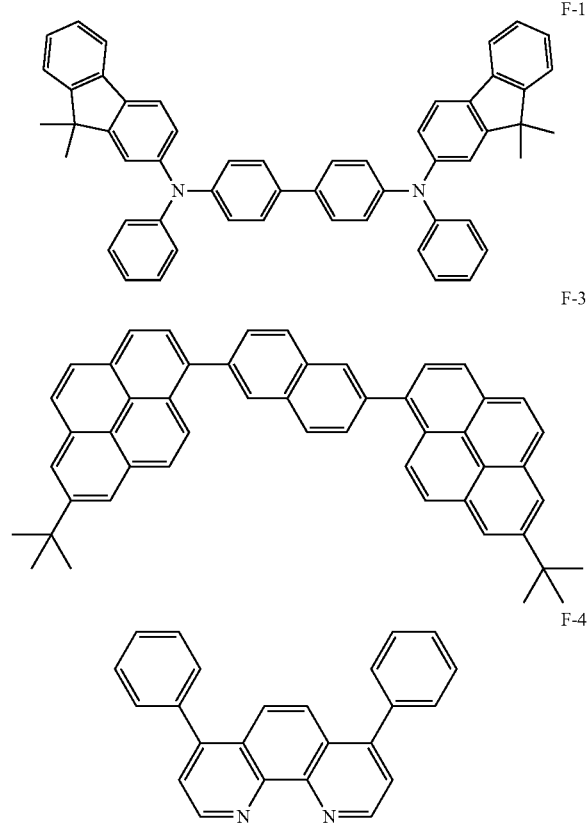

The current-voltage characteristic of each organic light-emitting device was measured with a pA meter 4140B produced by Hewlett-Packard Company and the luminance of emission was measured with BM7 produced by Topcon Corporation.

Table 5 below summarizes the guest compounds, the host compounds, the emission efficiency, and the application voltages of the organic light-emitting devices obtained in Examples 5 to 23.

TABLE 5

|  | Guest | F-2 | Emission efficiency (cd/A) | Voltage (V) |
| --- | --- | --- | --- | --- |
| EXAMPLE 5 | A1 | H2 | 4.1 | 4.2 |
| EXAMPLE 6 | A2 | H8 | 5.1 | 4.2 |
| EXAMPLE 7 | A3 | H8 | 5.2 | 4.1 |
| EXAMPLE 8 | A3 | H21 | 5.3 | 4.0 |
| EXAMPLE 9 | A7 | H21 | 5.6 | 4.1 |
| EXAMPLE 10 | A7 | H10 | 5.1 | 4.4 |
| EXAMPLE 11 | A11 | H11 | 5.0 | 4.3 |
| EXAMPLE 12 | A11 | H22 | 5.6 | 4.2 |

TABLE 5-continued

|  | Guest | F-2 | Emission efficiency (cd/A) | Voltage (V) |
| --- | --- | --- | --- | --- |
| EXAMPLE 13 | A12 | H28 | 5.4 | 4.1 |
| EXAMPLE 14 | A12 | H6 | 5.1 | 4.1 |
| EXAMPLE 15 | A22 | H8 | 5.0 | 4.2 |
| EXAMPLE 16 | A25 | H27 | 5.3 | 4.0 |
| EXAMPLE 17 | A35 | H7 | 4.5 | 4.0 |
| EXAMPLE 18 | A37 | H8 | 4.8 | 3.9 |
| EXAMPLE 19 | A44 | H5 | 4.2 | 4.1 |
| EXAMPLE 20 | A64 | H27 | 5.1 | 4.2 |
| EXAMPLE 21 | A67 | H18 | 5.3 | 3.9 |
| EXAMPLE 22 | A72 | H10 | 5.1 | 4.2 |
| EXAMPLE 23 | A81 | H10 | 4.7 | 4.0 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-324468, filed Dec. 19, 2008, which is hereby incorporated by reference herein in its entirety.

The invention claimed is:

1. A diacenaphtho[1,2-b:1',2'-k]chrysene derivative having a backbone represented by

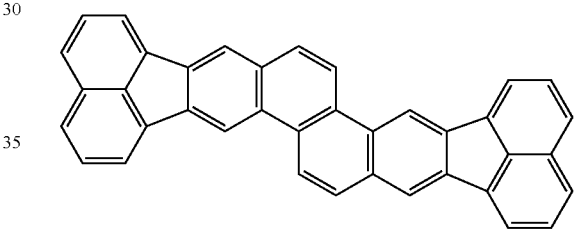

2. A diacenaphtho[1,2-b:1',2'-k]chrysene derivative represented by general formula (1):

(1)

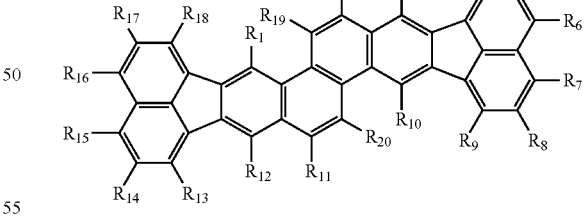

where $R_1$ to $R_{20}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

3. An organic light-emitting device comprising: a pair of electrodes and an organic compound layer interposed between the electrodes, wherein the organic compound layer contains the diacenaphthol [1,2-b:1', 2'-k]chrysene derivative according to claim 2.

4. The organic light-emitting device according to claim 3, wherein the organic compound layer is an emission layer.

5. An image-display apparatus comprising a display unit having the organic light-emitting device according to claim 4.

6. An image-capturing apparatus comprising a display unit having the organic light-emitting device according to claim 4.

7. An electrophotographic image-forming apparatus comprising: a photosensitive member; and a light source which emits light to the photosensitive member, wherein the light source has the organic light-emitting device according to claim 4.

8. A lighting apparatus comprising, a plurality of the organic light-emitting device according to claim 4 which are arranged in an in-plane direction.

9. A display apparatus comprising: a pixel; a pixel circuuit connected to the pixel; and signal and electrical current supply lines connected to the pixel circuit, wherein the pixel has the organic light-emitting device according to claim 4.

10. An apparatus comprising; a substrate; the organic light-emitting device according to claim 4, wherein the organic light-emitting device is provided on the substrate; and a color filter.

11. The organic light-emitting device according to claim 4, wherein the organic light-emitting device has another organic layer interposed between the electrodes, the another organic layer being located at least one of the anode side of the emission layer and the cathode side of the emission layer, and
  the another organic layer is at least one of a hole transport layer, a hole/exciton blocking layer, or an electron transport layer.

12. The organic light-emitting device according to claim 4, wherein the emission layer has a host material and a guest material and the organic compound is the host material or the guest material.

13. The organic light-emitting device according to claim 3, wherein the pair of electrodes is an anode and a cathode and the anode has a metal oxide, and, the metal oxide is one of tin oxide, zinc oxide, indium oxide, indium tin oxide (ITO), or zinc indium oxide.

14. The organic light-emitting device according to claim 3, wherein the pair of electrodes is an anode and a cathode and the anode has a metal oxide, and the metal oxide is indium tin oxide (ITO).

15. The electroohotographic image-forming apparatus according to claim 7, wherein the light source has a plurality of the organic light-emitting devices whihc is arranged into lines.

* * * * *